United States Patent
Yen et al.

(10) Patent No.: US 9,698,357 B2
(45) Date of Patent: Jul. 4, 2017

(54) PHENANTHROLINE-BASED COMPOUND AND USE THEREOF

(71) Applicant: LUMINESCENCE TECHNOLOGY CORPORATION, Hsin-Chu (TW)

(72) Inventors: Feng Wen Yen, Hsin Chu (TW); Cheng Hao Chang, Hsin-Chu (TW); Chin Min Teng, Hsin-Chu (TW); I Feng Lin, Hsin-Chu (TW)

(*) Notice: Subject to any disclaimer, the term of this patent is extended or adjusted under 35 U.S.C. 154(b) by 191 days.

(21) Appl. No.: 14/555,729

(22) Filed: Nov. 28, 2014

(65) Prior Publication Data
US 2016/0155949 A1 Jun. 2, 2016

(51) Int. Cl.
| | | |
|---|---|---|
| H01L 51/50 | (2006.01) | |
| H01L 51/00 | (2006.01) | |
| C07D 471/04 | (2006.01) | |
| C09K 11/06 | (2006.01) | |
| H05B 33/20 | (2006.01) | |

(52) U.S. Cl.
CPC ........ H01L 51/0072 (2013.01); C07D 471/04 (2013.01); C09K 11/06 (2013.01); H01L 51/0054 (2013.01); H05B 33/20 (2013.01); H01L 51/0085 (2013.01); H01L 51/5016 (2013.01); H01L 51/5096 (2013.01)

(58) Field of Classification Search
None
See application file for complete search history.

(56) References Cited

U.S. PATENT DOCUMENTS

| | | |
|---|---|---|
| 5,393,614 A | 2/1995 | Nakada |
| 7,119,204 B2 | 10/2006 | Lecloux et al. |
| 7,282,586 B1 | 10/2007 | Yen et al. |
| 7,754,348 B2 | 7/2010 | Yen |
| 7,982,213 B2 | 7/2011 | Okajima et al. |
| 8,114,529 B2 | 2/2012 | Kitazawa et al. |

FOREIGN PATENT DOCUMENTS

KR  2012-072784  * 12/2010 ............. H02L 51/54

* cited by examiner

*Primary Examiner* — Gregory Clark

(57) ABSTRACT

The present invention discloses a novel phenanthroline-based compound is represented by the following formula(I), the organic EL device employing the phenanthroline-based compound as hole blocking material/electron transport material or phosphorescent host can display good performance.

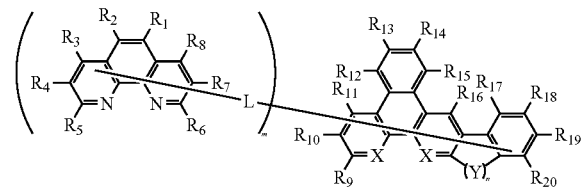

formula(I)

L, m, n, X, Y and $R_1$ to $R_{20}$ each have the same meaning as described in the present invention.

12 Claims, 1 Drawing Sheet

| 13 | — | metal electrode |
| 12 | — | electron injection layer |
| 11 | — | electron transport layer |
| 10 | — | hole blocking layer |
| 9  | — | emitting layer |
| 8  | — | hole transport layer |
| 7  | — | hole injection layer |
| 6  | — | transparent electrode |

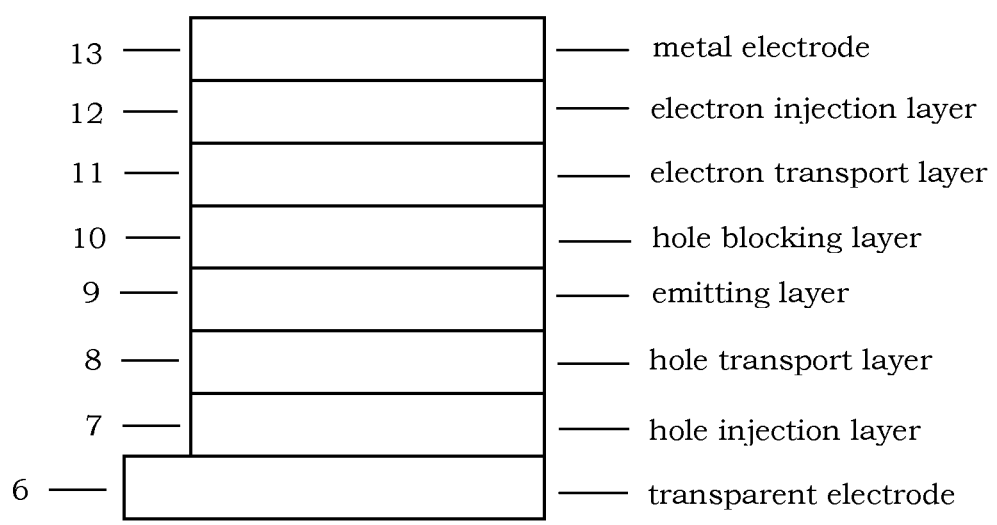

PHENANTHROLINE-BASED COMPOUND AND USE THEREOF

FIELD OF INVENTION

The present invention generally relates to a novel phenanthroline-based compound and organic electroluminescent (herein referred to as organic EL) device using the phenanthroline-based compound. More specifically, the present invention relates to the phenanthroline-based compound having general formula (I), an organic EL device employing the phenanthroline-based compound as hole blocking material/electron transport material or phosphorescent host.

BACKGROUND OF THE INVENTION

Organic electroluminescent (organic EL) is a light-emitting diode (LED) in which the emissive layer is a film made by organic compounds which emits light in response to an electric current. The emissive layer of organic compound is sandwiched between two electrodes. Organic EL is applied in flat panel displays due to their high illumination, low weight, ultra-thin profile, self-illumination without back light, low power consumption, wide viewing angle, high contrast, simple fabrication methods and rapid response time.

The first observation of electroluminescence in organic materials were in the early 1950s by Andre Bernanose and co-workers at the Nancy-University in France. Martin Pope and his co-workers at New York University first observed direct current (DC) electroluminescence on a single pure crystal of anthracene and on anthracene crystals doped with tetracene under vacuum in 1963.

The first diode device was reported by Ching W. Tang and Steven Van Slyke at Eastman Kodak in 1987. The device used a two-layer structure with separate hole transporting and electron transporting layers resulted in reduction in operating voltage and improvement of the efficiency, that led to the current era of organic EL research and device production.

Typically organic EL is composed of layers of organic materials situated between two electrodes, which include a hole transporting layer (HTL), an emitting layer (EML), an electron transporting layer (ETL). The basic mechanism of organic electroluminescence involves the injection of the carrier, transport, recombination of carriers and exciton formed to emit light. When an external voltage is applied to an organic light-emitting device, electrons and holes are injected from a cathode and an anode, respectively, electrons will be injected from a cathode into a LUMO (lowest unoccupied molecular orbital) and holes will be injected from an anode into a HOMO (highest occupied molecular orbital). When the electrons recombine with holes in the emitting layer, excitons are formed and then emit light. When luminescent molecules absorb energy to achieve an excited state, an exciton may either be in a singlet state or a triplet state depending on how the spins of the electron and hole have been combined. 75% of the excitons form by recombination of electrons and holes to achieve a triplet excited state. Decay from triplet states is spin forbidden, Thus, a fluorescence electroluminescent device has only 25% internal quantum efficiency. In contrast to fluorescence electroluminescent device, phosphorescent organic light-emitting diodes make use of spin-orbit interactions to facilitate intersystem crossing between singlet and triplet states, thus obtaining emission from both singlet and triplet states and the internal quantum efficiency of electroluminescent devices from 25% to 100%.

Recently, a new type of fluorescent organic EL incorporating mechanism of thermally activated delayed fluorescence (TADF) has been developed by Adachi and coworkers is a promising way to obtain a high efficiency of exciton formation by converting spin-forbidden triplet excitons up to the siglet level by the mechanism of reverse intersystem crossing (RISC.

The phosphorescent organic EL utilizes both triplet and singlet excitons. Cause of longer lifetime and the diffusion length of triplet excitons compared to those of singlet excitons, the phosphorescent organic EL generally need an additional hole blocking layer (HBL) between the emitting layer (EML) and the electron-transporting layer (ETL) or the electron-transporting layer with hole blocking ability instead of typical ETL. The purpose of the use of HBL or HBETL is to confine the recombination of injected holes and electrons and the relaxation of created excitons within the EML, hence the device's efficiency can be improved. To meet such roles, the hole blocking materials must have HOMO (highest occupied molecular orbital) and LUMO (lowest unoccupied molecular orbital) energy levels suitable to block hole transport from the EML to the ETL and to pass electrons from the ETL to the EML, in addition, the good thermal and electrochemical stability of the materials are also needed.

Currently, 2,9-dimethyl-4,7-diphenyl-1,10-phenanthroline (BCP), bathophenanthroline (Bphen) have been used as the typical materials for the HBL and HBETL of phosphorescent OLED. However, phenanthroline derivatives exhibit lower Tg (Bphen: 55° C., BCP: 65° C.), lower heat-resistant (Td: Weight loss <0.5% at 240° C. for Bphen and 260° C. for BCP). It's difficult to operate under deposition process and its devices show lower stability and short half-life time. U.S. Pat. No. 7,119,204 disclose a series of substituted-phenanthroline derivatives, as electron-transporting materials. U.S. Pat. No. 7,282,586 disclose a specific phenanthroline derivative 2,9-bis(5-(biphenyl-4-yl)-1,3,4-oxadiazol-2-yl)-1,10-phenanthroline, as an electron transporting material, compare with conventional 2,9-dimethyl-4,7-diphenyl-1,10-phenanthroline (BCP), the drive voltage is decreased from 8V to 7V at 2000 cd/m$^2$, and higher current efficiency is achieved. U.S. Pat. No. 7,754,348 disclose a series of 2,9-substituted phenanthroline derivatives as electron transporting material, higher operate live time and higher luminance than comparable example 1-3 and Alq3 has also been achieved at a driving voltage of 5V. U.S. Pat. No. 7,982,213 disclose a series of aryl substituted phenanthroline, a phosphorescent organic EL using the phenanthroline compound as HBETL provided high efficiency and a high luminance and has a high long-term durability. U.S. Pat. No. 8,114,529 disclose a series of bis-phenanthroline skeleton compounds, by using the phenanthroline compounds as HBETL, phosphorescent organic EL having low driving voltage and excellent durability.

There continues to be a need for organic EL materials which is able to efficiently transport electrons and block holes, with good thermal stability and high emitting efficiency. According to the reasons described above, the present invention has the objective of resolving such problems of the prior-art and offering a light emitting device which is excellent in its thermal stability, high luminance efficiency, high luminance and long half-life time. The present invention disclose a novel phenanthroline-based compound having general formula (I), used as hole blocking material/ electron transport material or phosphorescent host have good charge carrier mobility and excellent operational durability can lower driving voltage and power consumption, increasing efficiency and half-life time of organic EL device.

SUMMARY OF THE INVENTION

In accordance with the present invention, the phenanthroline-based compound for hole blocking material/electron transport material or phosphorescent host and their use for organic EL device are provided. The phenanthroline-based compound can overcome the drawbacks of the conventional materials like as shorter half-life time, lower efficiency and higher power consumption.

An object of the present invention is to provide the phenanthroline-based compound which can be used as hole blocking material/electron transport material for organic EL device and can efficiently confine excitons to transfer to electron transport layer.

An object of the present invention is to provide the phenanthroline-based compound which can be used as phosphorescent host material of emitting layer for organic EL device.

Another object of the present invention is to apply the he phenanthroline-based compound for organic EL device and improve the half-life time, lower driving voltage, lower power consumption and increase the efficiency.

The present invention has the economic advantages for industrial practice. Accordingly the present invention, the phenanthroline-based compound which can be used for organic EL device is disclosed. The mentioned the phenanthroline-based compound is represented by the following formula (I):

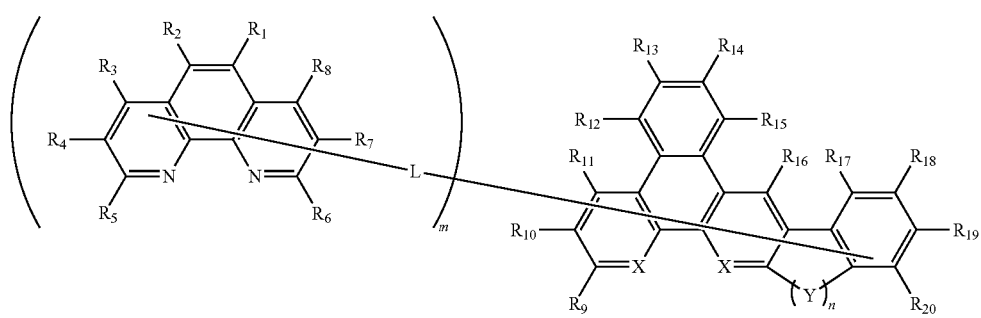

formula(I)

Wherein L represent a single bond, a substituted or unsubstituted arylene group having 6 to 30 ring carbon atoms, or a substituted or unsubstituted heterarylene group having 3 to 30 ring carbon atoms. m represent an integer of 1 to 3. n represent an integer of 0 or 1, X represent carbon or nitrogen atom. Y is a divalent bridge selected from the atom or group consisting from 0, S, $C(R_{21})(R_{22})$, N—HAr, $Si(R_{23})(R_{24})$. $R_1$ and $R_2$ may be bonded each other to form a benzene ring and adjacent to phenanthroline skeleton to form a substituted or unsubstituted benzo[f][1,10]phenanthroline ring. $R_1$ to $R_{24}$ independently selected from the group consisting of a hydrogen atom, alkyl group having 1 to 20 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 3 to 30 carbon atoms. HAr represent a substituted or unsubstituted heteroaryl group having 3 to 40 carbon atoms.

According to the present invention, when m and n represent 1, L represent a single bond or a substituted or unsubstituted phenylene group and is bonded to the phenanthroline skeleton at the $R_5$ position and to the notriphenylene skeleton at one of the $R_9$, $R_{10}$, $R_{18}$ and $R_{19}$ position. Y represent $C(R_{21})(R_{22})$, $R_1$ to $R_{22}$ and X each have the same meaning as that in the formula(I) . . . . The phenanthroline-based compound according to the above-mentioned formula (I) is preferably represented by the following formula (I-1) ~formula (I-4) which are eligibly used as electron transport material or hole blocking material for organic EL device.

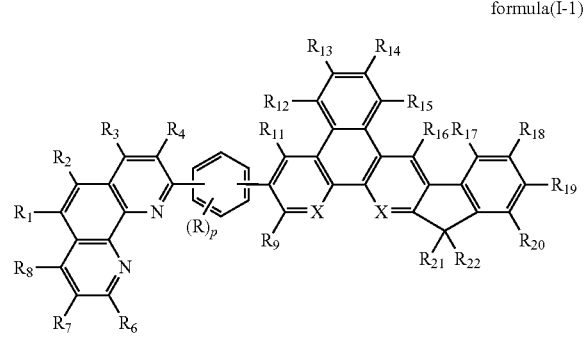

formula(I-1)

-continued

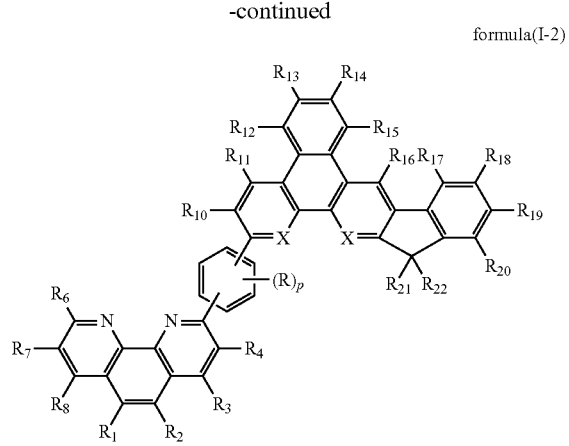

formula(I-2)

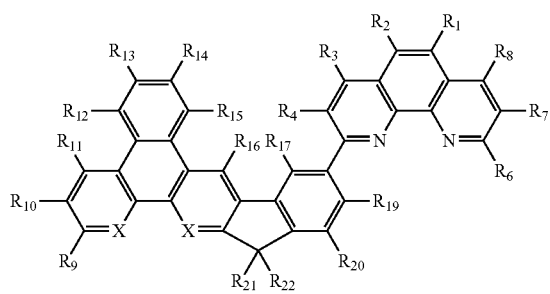

formula(I-3)

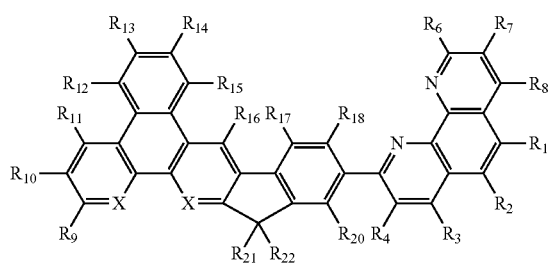

formula(I-4)

wherein R have the same meaning as $R_1$, p represent an integer of 0 to 4.

According to the present invention, when m and n represent 1, L represent a single bond, and is bonded to the phenanthroline skeleton at the $R_5$ position and to the indenotriphenylene skeleton at one of the $R_{18}$ and $R_{19}$ position. Y represent N-HAr, $R_1$ to $R_{20}$ and X each have the same meaning as that in the formula(I). The phenanthroline-based compound according to the above-mentioned formula(I) is preferably represented by the following formula (I-5)~formula(I-6) which are eligibly used as phosphorescent host for organic EL device.

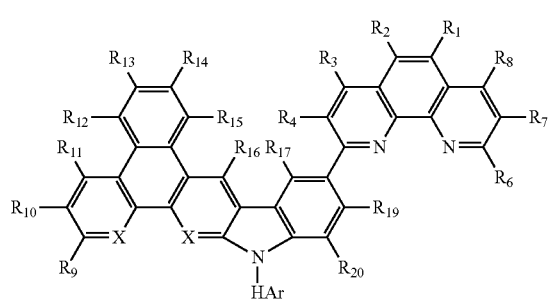

formula(I-5)

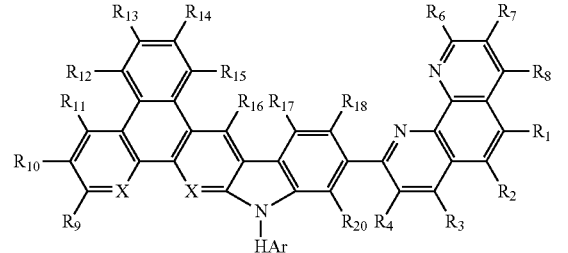

formula(I-6)

wherein preferably HAr represent a substituted or unsubstituted carbazolyl group, a substituted or unsubstituted biscarbazolyl group, a substituted or unsubstituted dibenzofuranyl group, a substituted or unsubstituted dibenzothiophenyl group. a substituted or unsubstituted triazinyl group, a substituted or unsubstituted diazinyl group.

BRIEF DESCRIPTION OF THE DRAWINGS

FIG. 1 show one example of organic EL device in the present invention. 6 is transparent electrode, 13 is metal electrode, 7 is hole injection layer which is deposited onto 6, 8 is hole transporting layer which is deposited onto 7, 9 is fluorescent or phosphorescent emitting layer which is deposited onto 8, 10 is hole blocking layer which is deposited onto 9, 11 is electron transporting layer which is deposited onto 10, 12 is electron injection layer which is deposited on to 10.

DESCRIPTION OF THE PREFERRED EMBODIMENTS

What probed into the invention is the phenanthroline-based compound and organic EL device using the phenanthroline-based compound. Detailed descriptions of the production, structure and elements will be provided in the following to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

Definition

In a first embodiment of the present invention, the phenanthroline-based compound which can be used as hole blocking material/electron transport material or phosphorescent host for organic EL device are disclosed. The mentioned material are represented by the following formula (I):

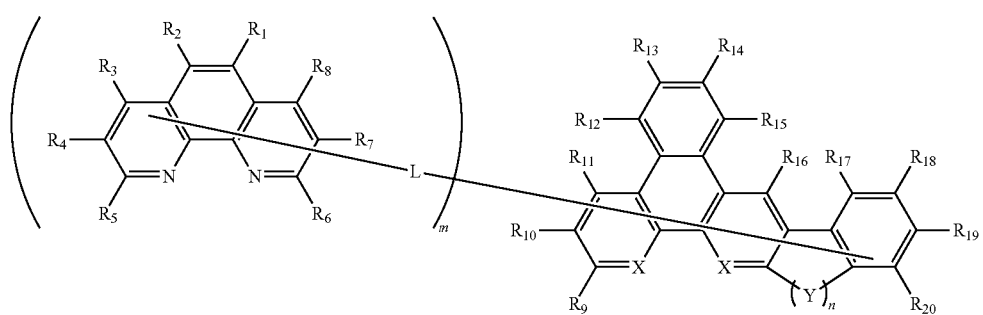

formula(I)

Wherein L represent a single bond, a substituted or unsubstituted arylene group having 6 to 30 ring carbon atoms, or a substituted or unsubstituted hetarylene group having 3 to 30 ring carbon atoms. m represent an integer of 1 to 3. n represent an integer of 0 or 1, X represent carbon or nitrogen atom. Y is a divalent bridge selected from the atom or group consisting from O, S, $C(R_{21})(R_{22})$, N—HAr, $Si(R_{23})(R_{24})$. $R_1$ and $R_2$ may be bonded each other to form a benzene ring and adjacent to phenanthroline skeleton to form a substituted or unsubstituted benzo[f][1,10]phenanthroline ring. $R_1$ to $R_{24}$ independently selected from the group consisting of a hydrogen atom, alkyl group having 1 to 20 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 3 to 30 carbon atoms. HAr represent a substituted or unsubstituted heteroaryl group having 3 to 40 carbon atoms.

According to the present invention, when m and n represent 1, L represent a single bond or a substituted or unsubstituted phenyl group and is bonded in the 5nd position of the phenanthroline skeleton and one of the 9nd, 10nd, 18nd, 19nd position of indenotriphenylene skeleton. Y represent $C(R_{21})(R_{22})$, $R_1$ to $R_{22}$ and X each have the same meaning as that in the formula (I). The phenanthroline-based compound according to the above-mentioned formula (I) is preferably represented by the following formula (I-1)~formula (I-4) which are eligibly used as electron transport material or hole blocking material for organic EL device.

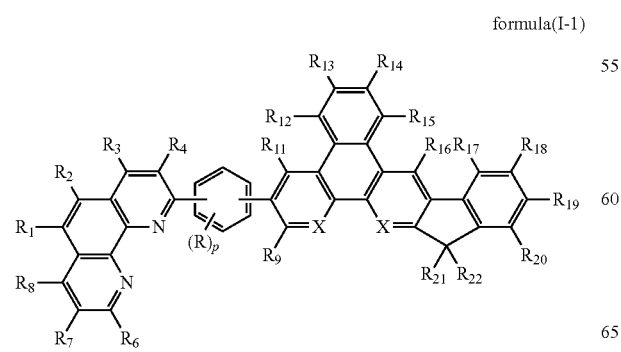

formula(I-1)

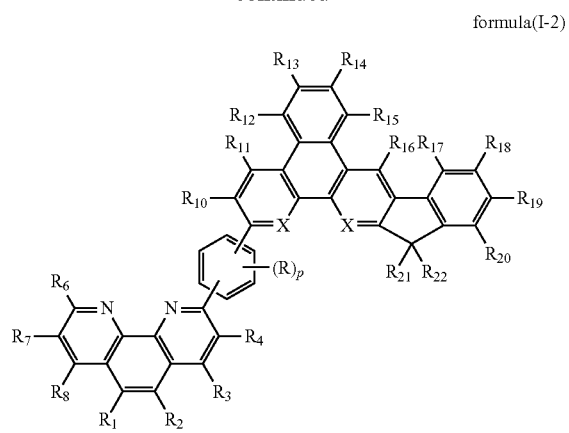

formula(I-2)

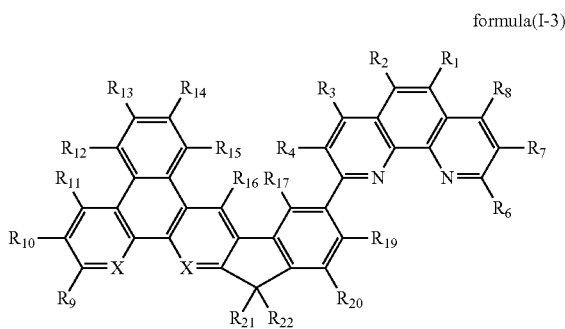

formula(I-3)

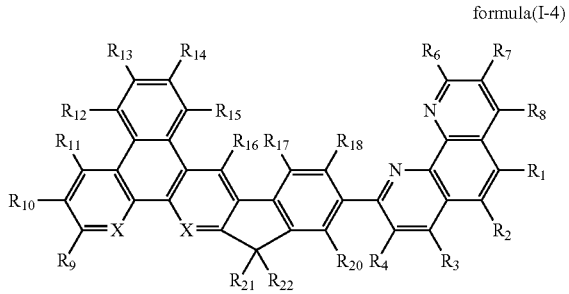

formula(I-4)

According to the present invention, when m and n represent 1, L represent a single bond or a substituted or unsubstituted phenyl group and is bonded in the 5nd position of the phenanthroline skeleton and one of the 9nd, 10nd position of indenotriphenylene skeleton. Y represent N—HAr, $R_1$ to $R_2O$ and X each have the same meaning as that in the formula (I). The phenanthroline-based compound according to the above-mentioned formula (I) is preferably represented by the following formula (I-5)~formula (I-6) which are eligibly used as phosphorescent host for organic EL device.

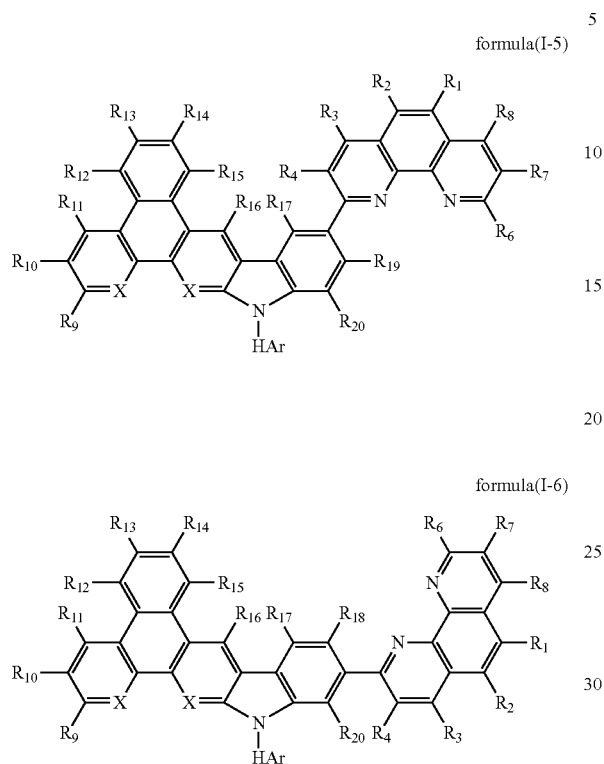

formula(I-5)

formula(I-6)

wherein preferably HAr represent a substituted or unsubstituted carbazolyl group, a substituted or unsubstituted biscarbazolyl group, a substituted or unsubstituted dibenzofuranyl group, a substituted or unsubstituted dibenzothiophenyl group. a substituted or unsubstituted triazinyl group, a substituted or unsubstituted diazinyl group and is selected from the group consisting of the followings:

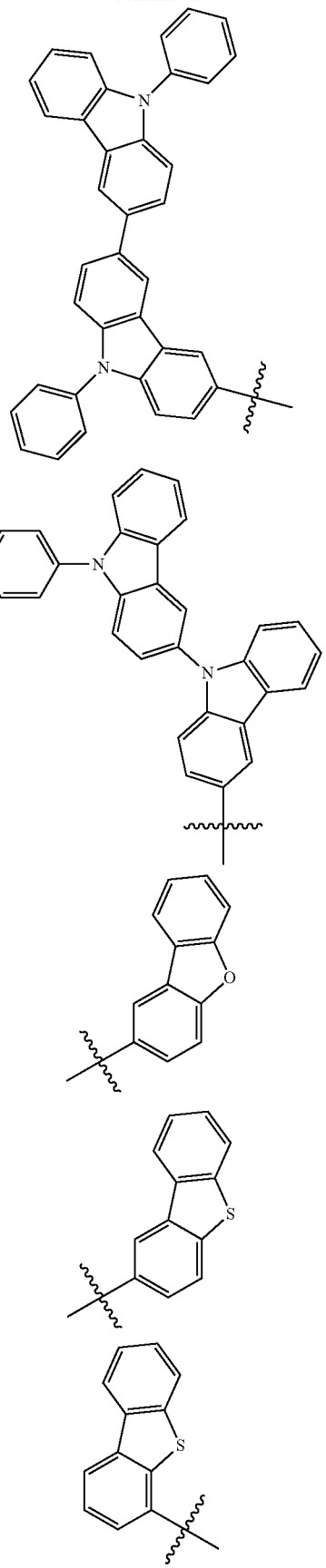

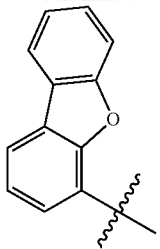
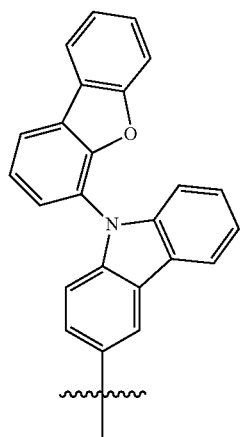
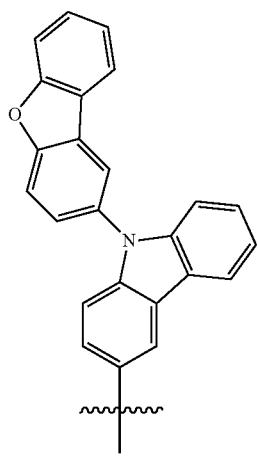
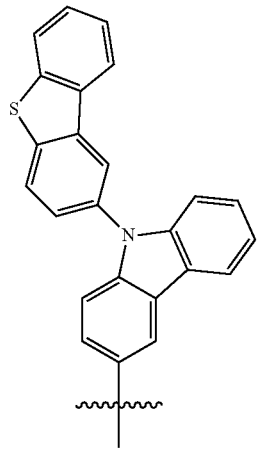
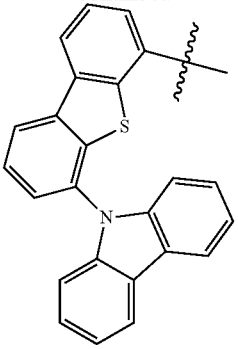
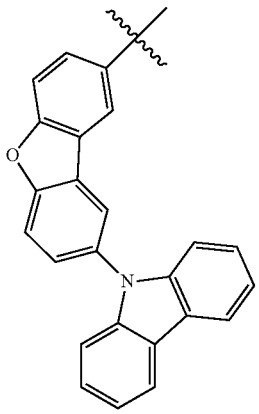
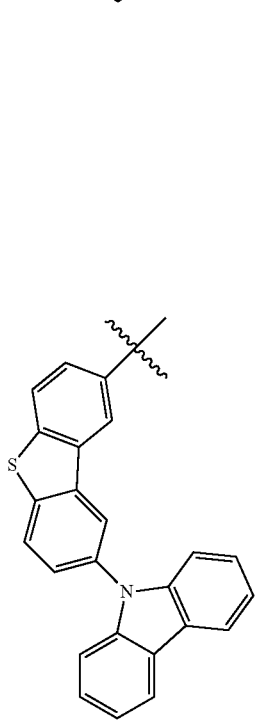

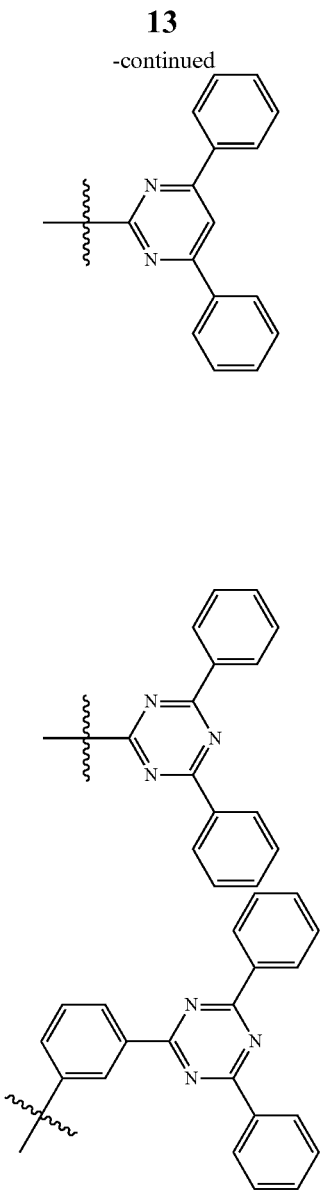
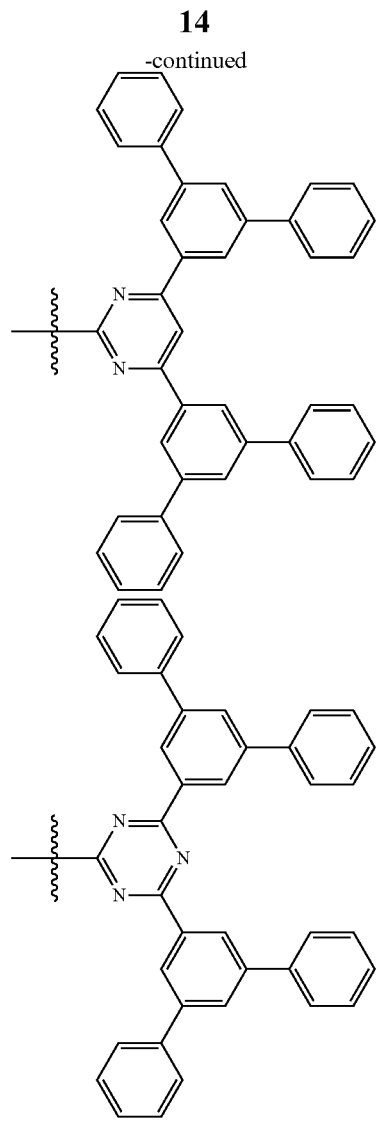
In this embodiment, some phenanthroline-based compounds are shown below:
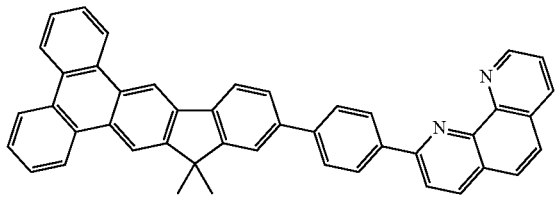
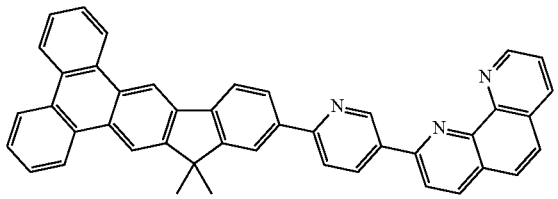
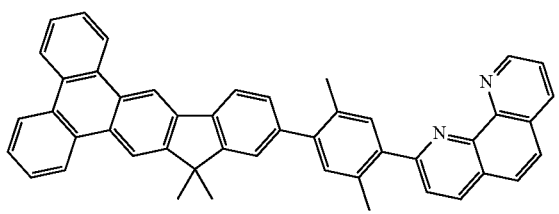
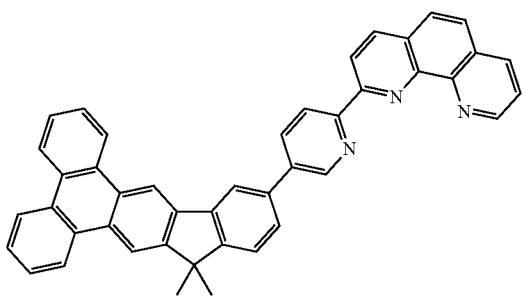

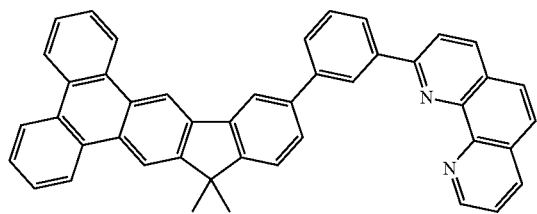
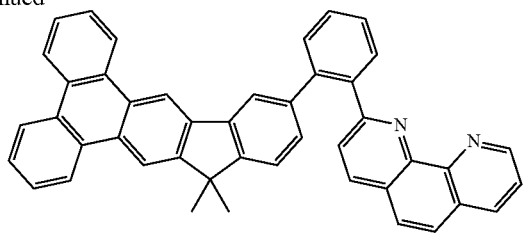
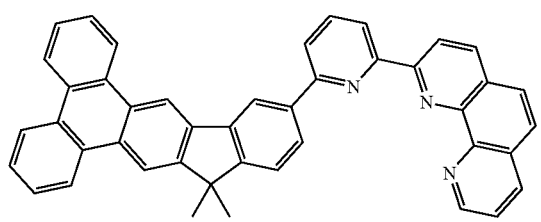
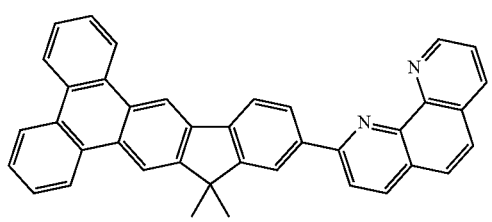
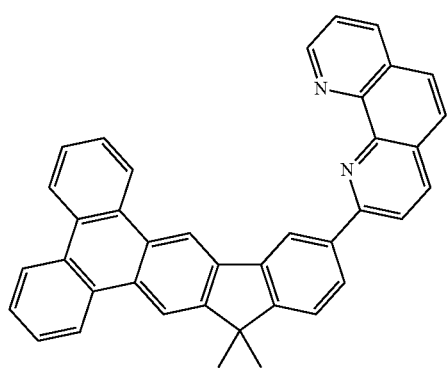
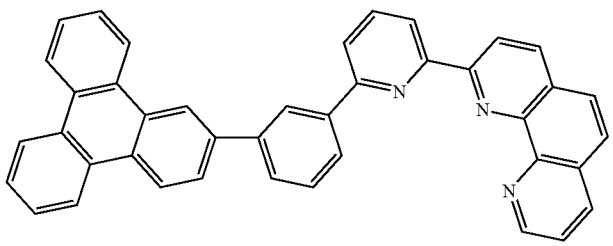
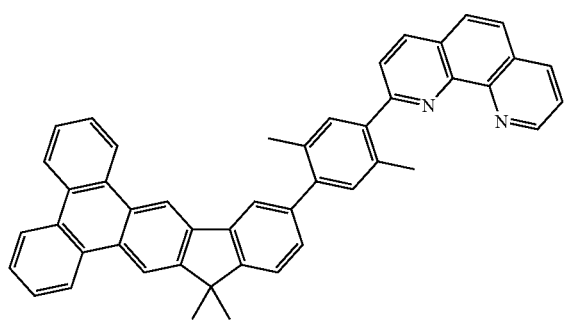
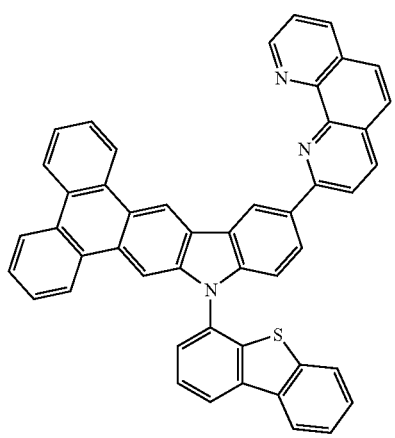

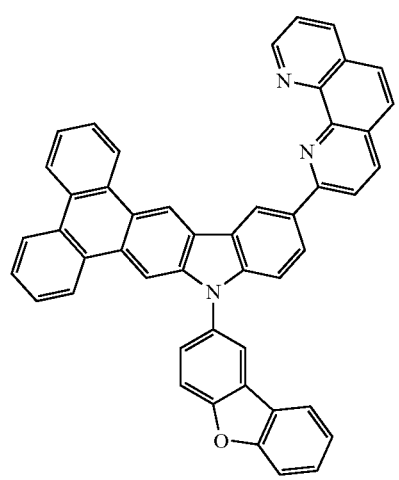
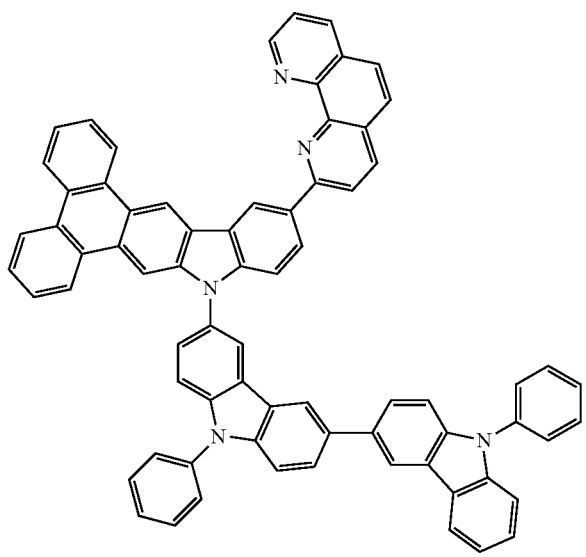
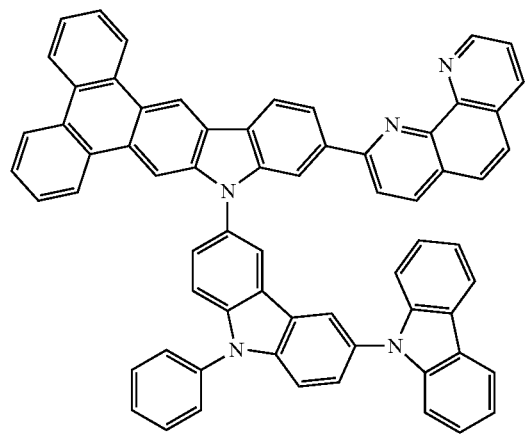
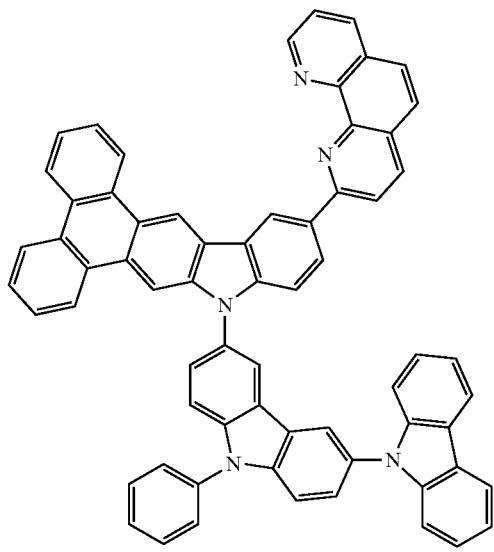
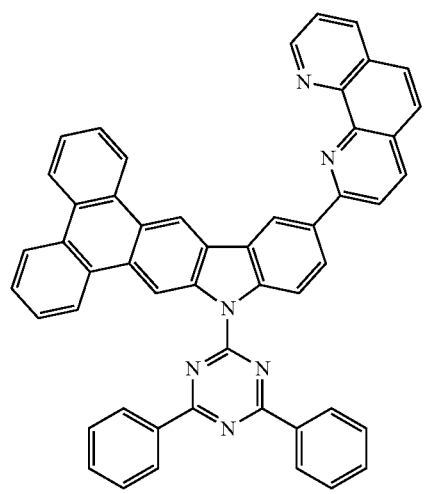
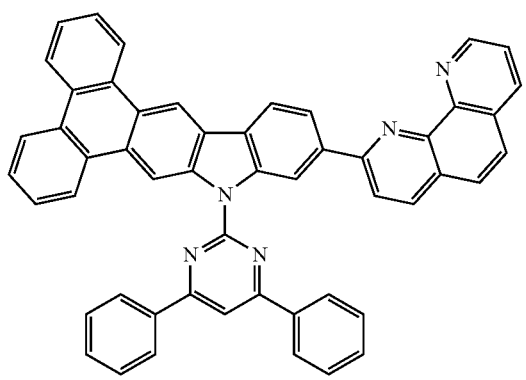

-continued
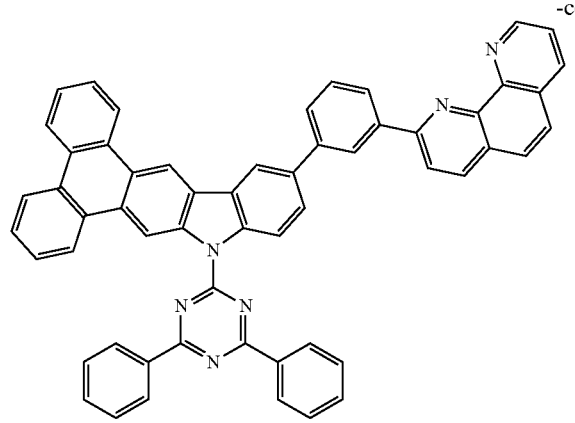
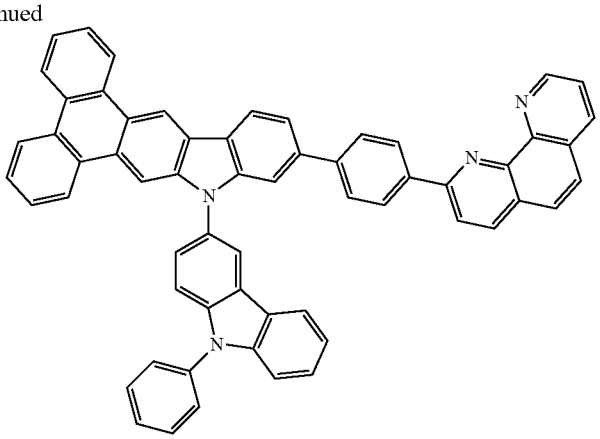
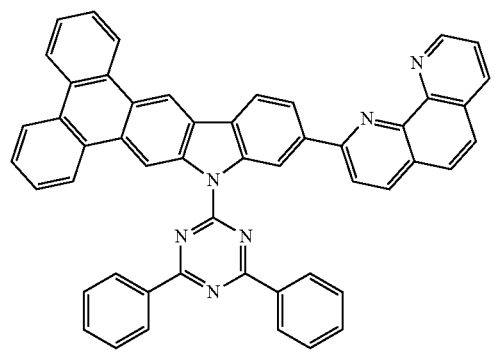
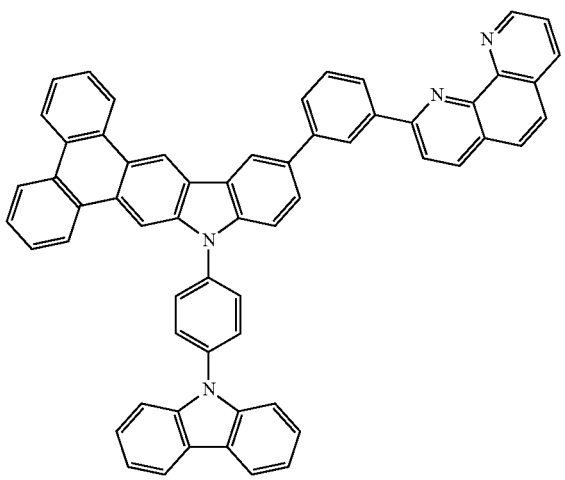
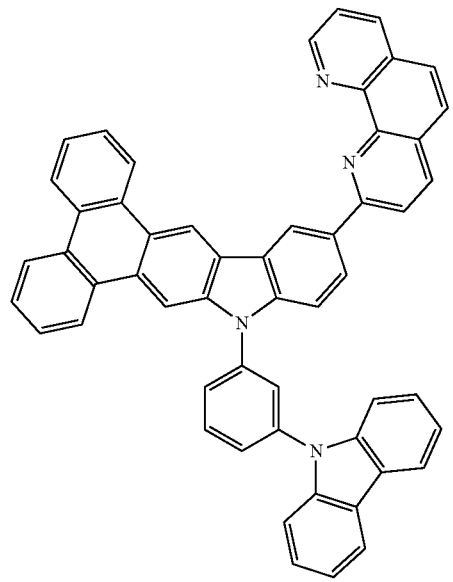
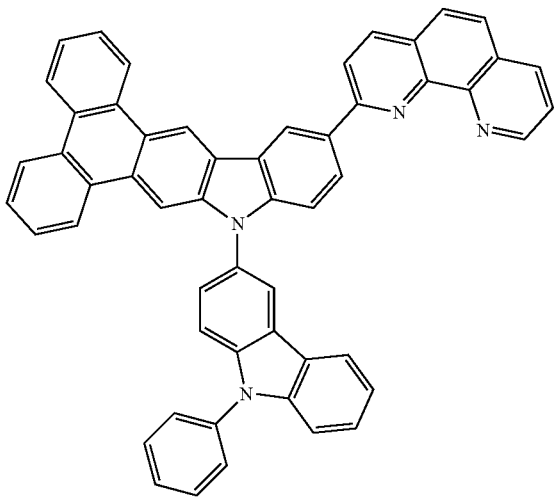

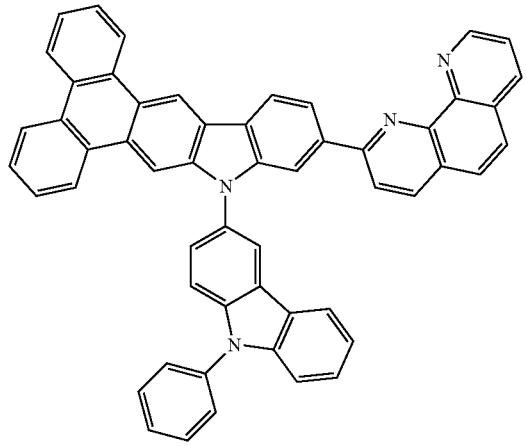
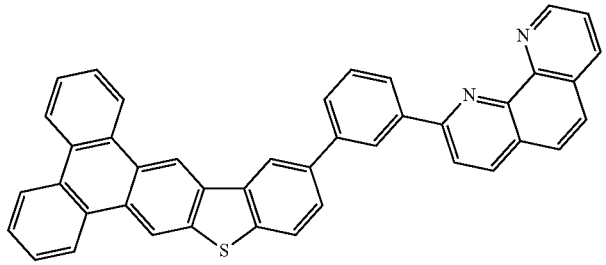
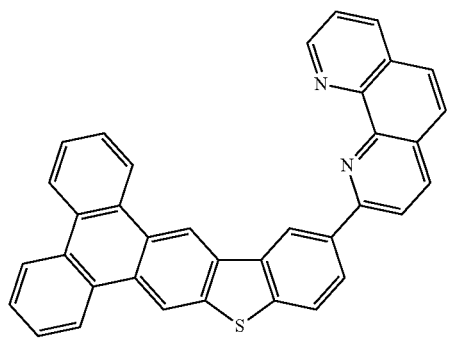
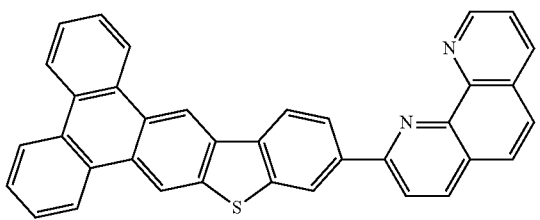
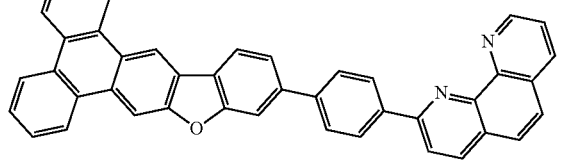
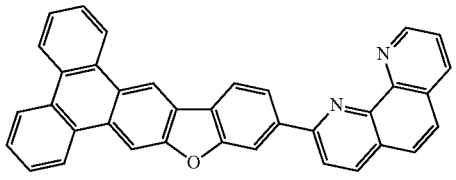
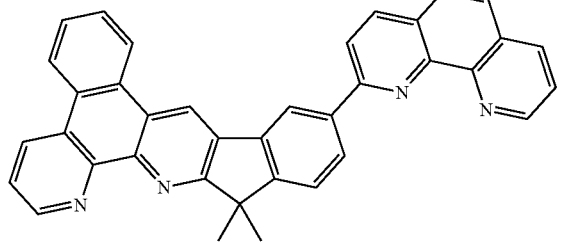
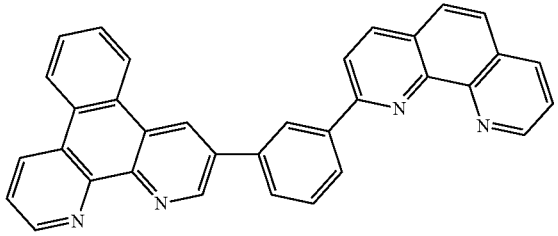
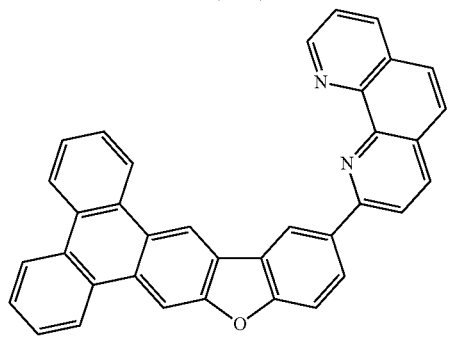
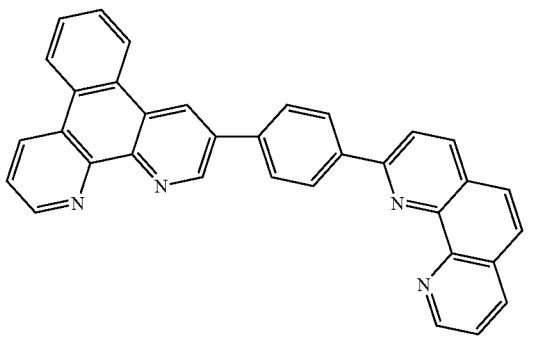

-continued
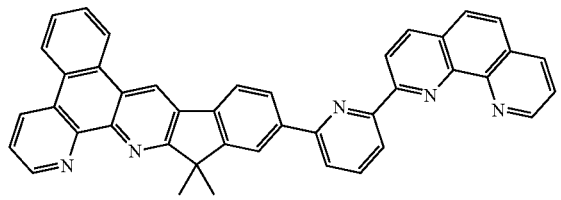
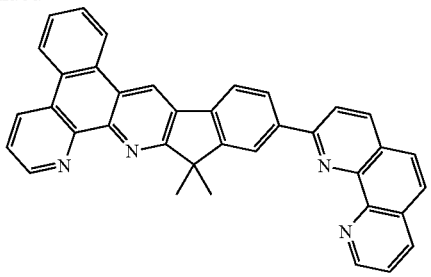
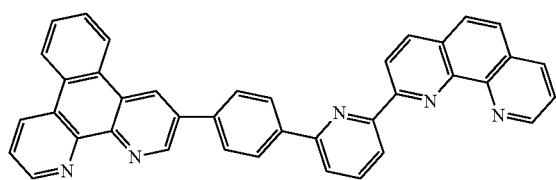
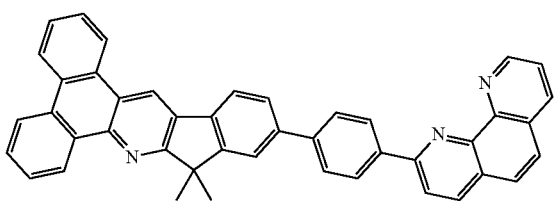
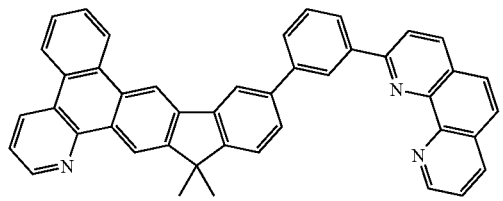
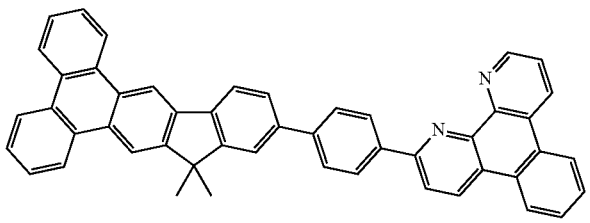
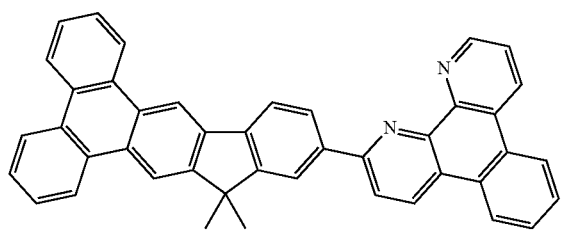
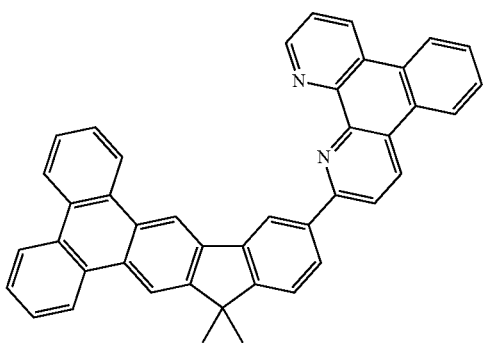
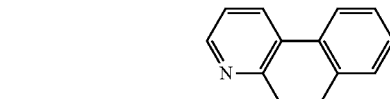
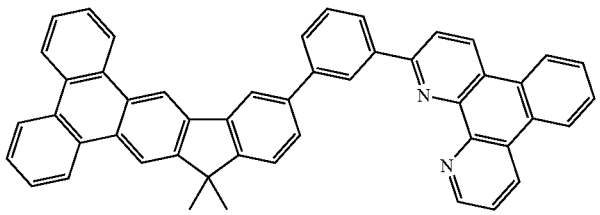
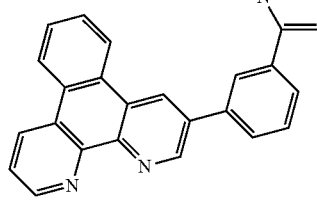
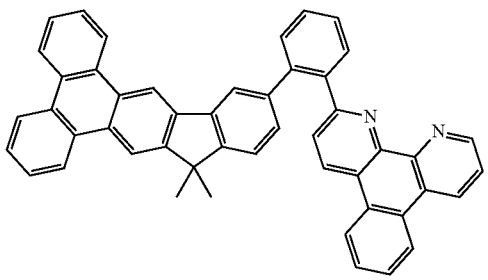

-continued
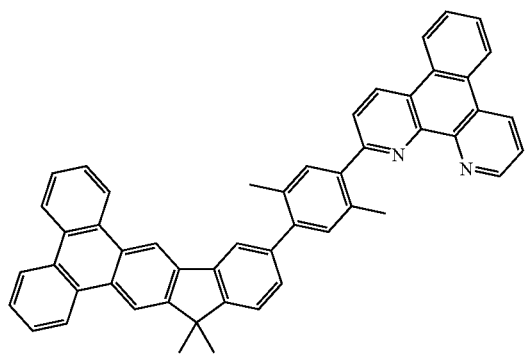
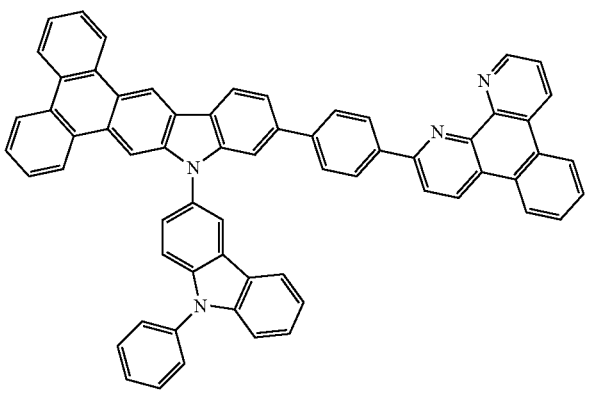
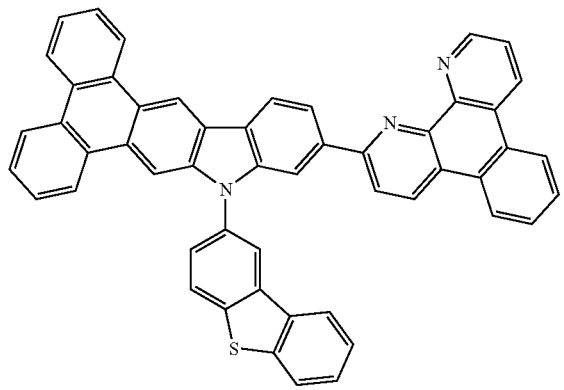
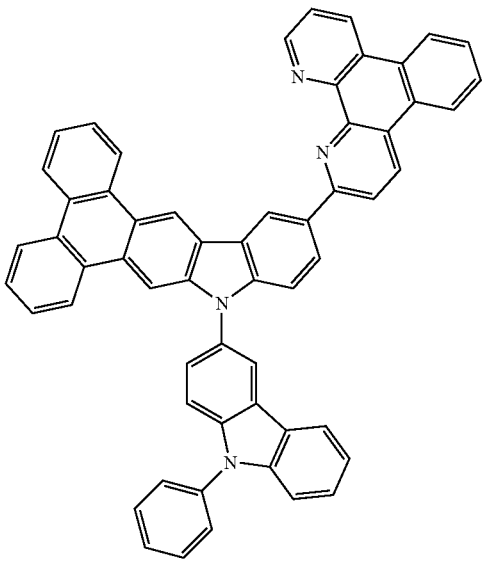
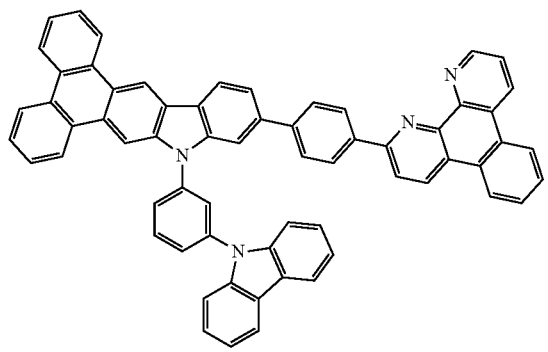
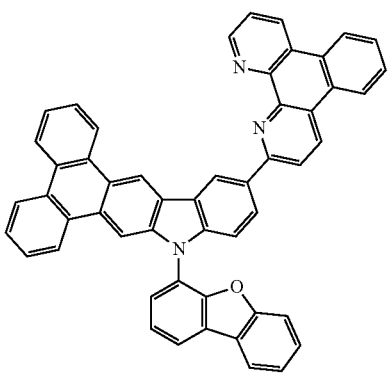
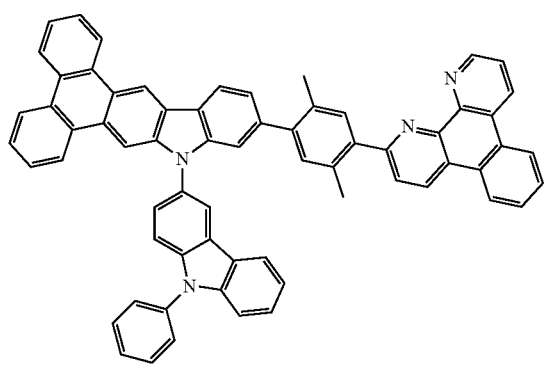
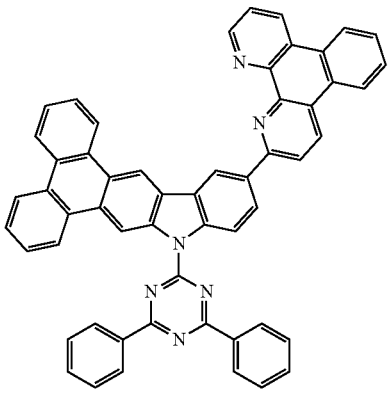

-continued
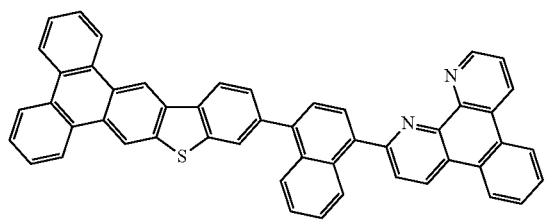
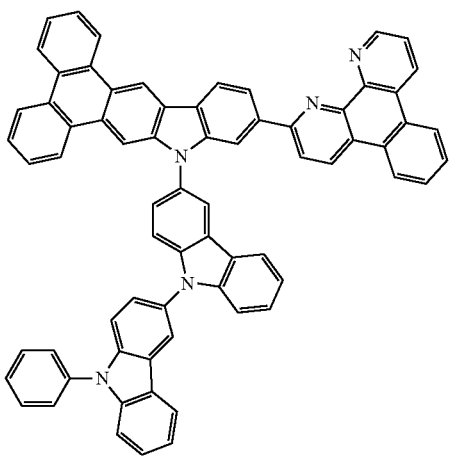
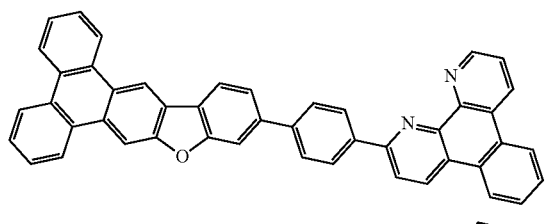
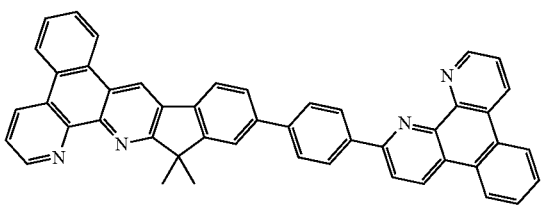
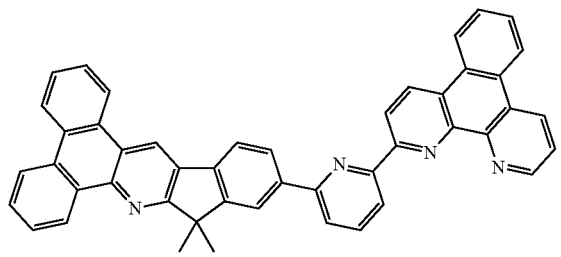
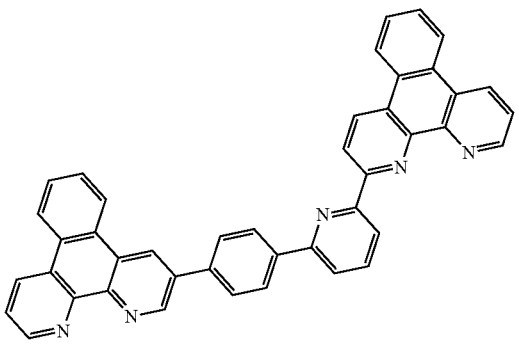
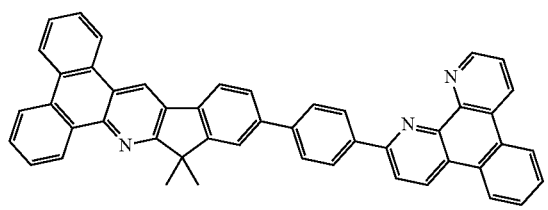
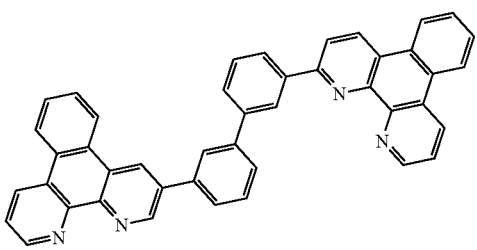
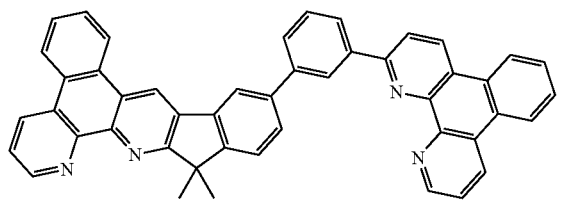
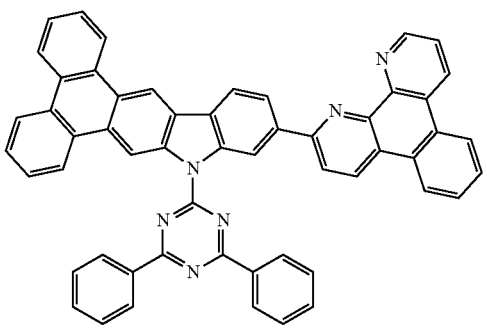

-continued
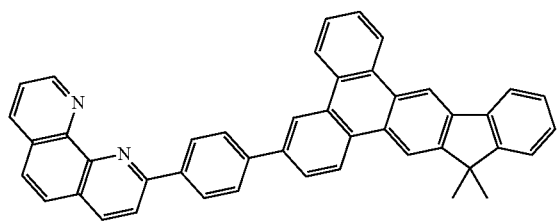 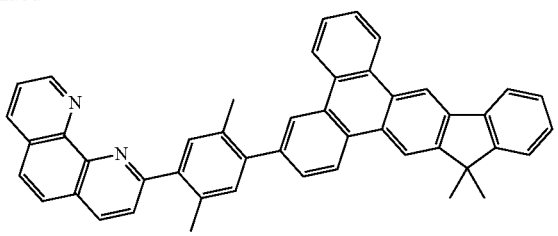
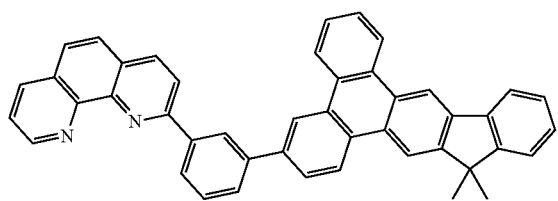 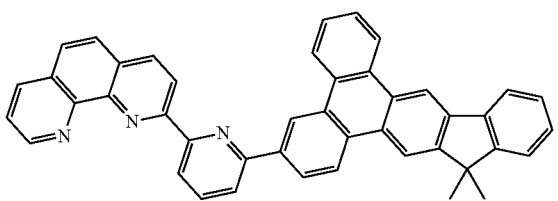
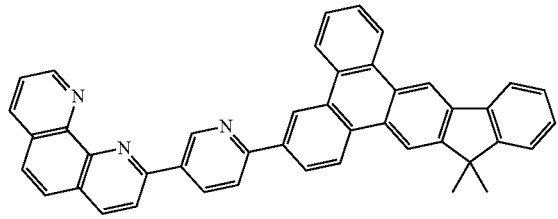 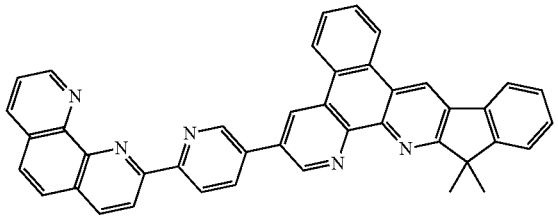
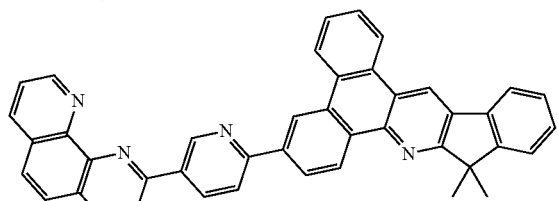 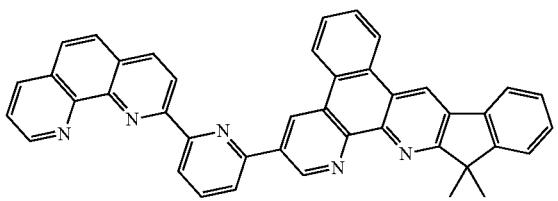
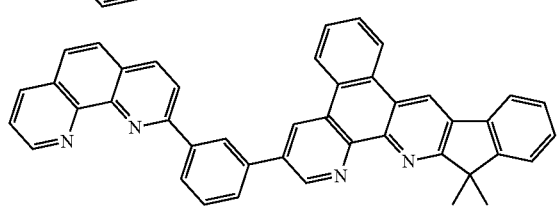 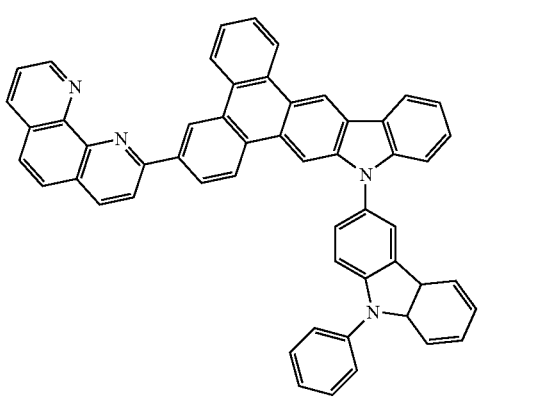
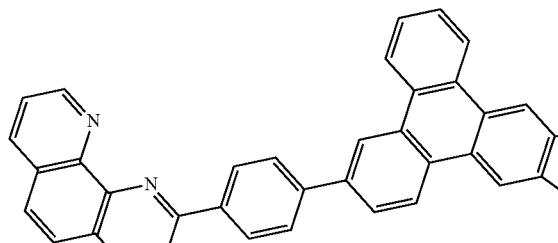
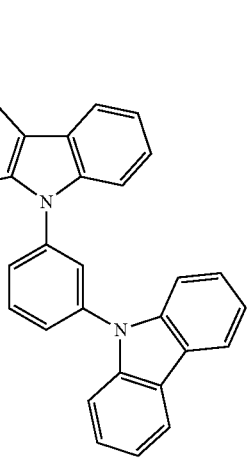

-continued
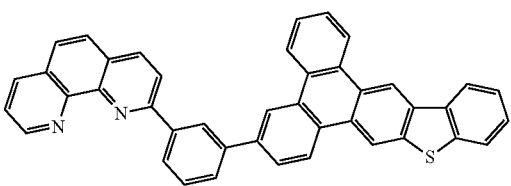
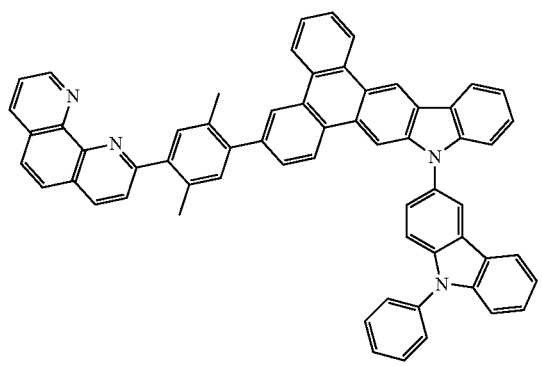
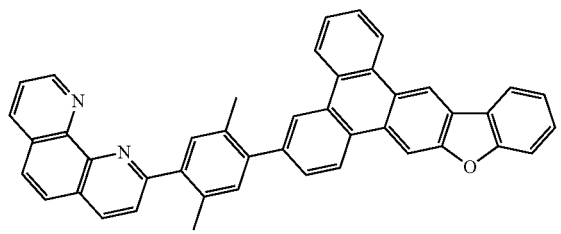
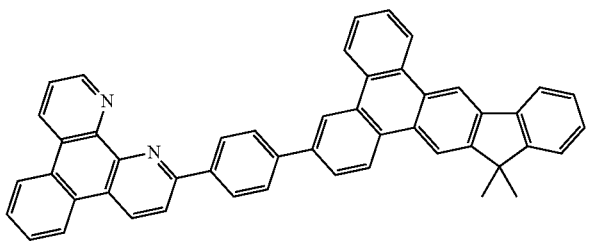
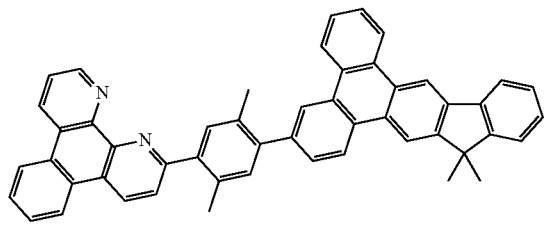
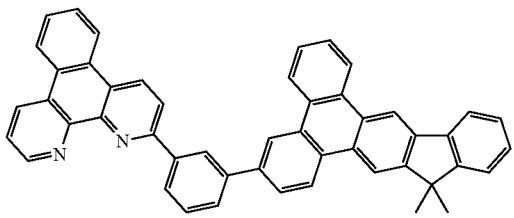
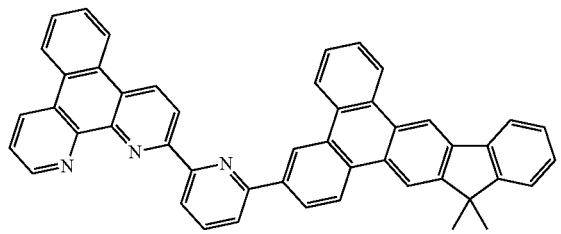
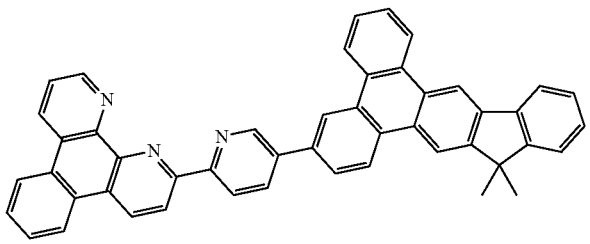
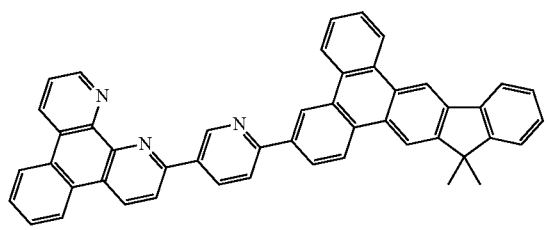
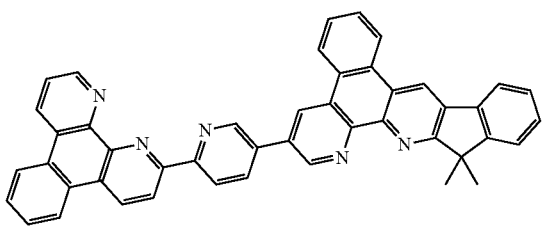
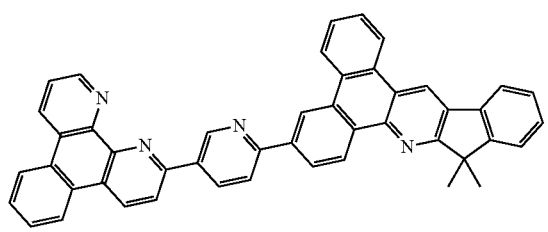
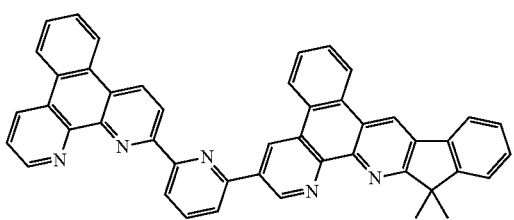

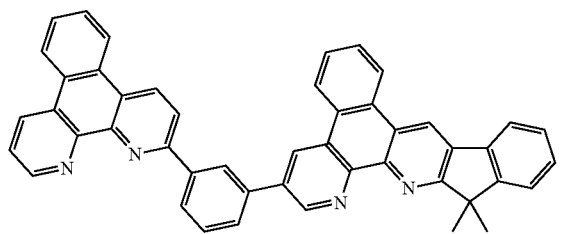
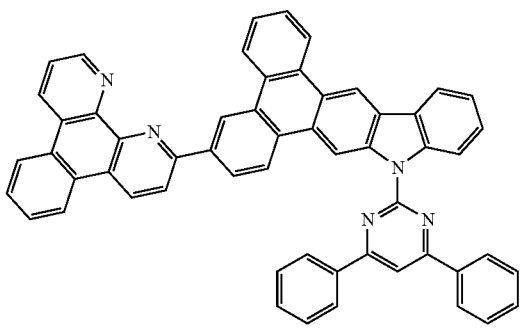
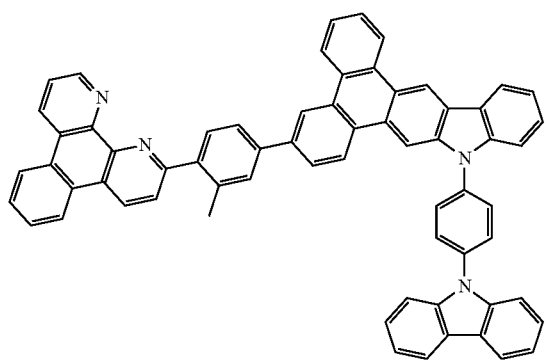
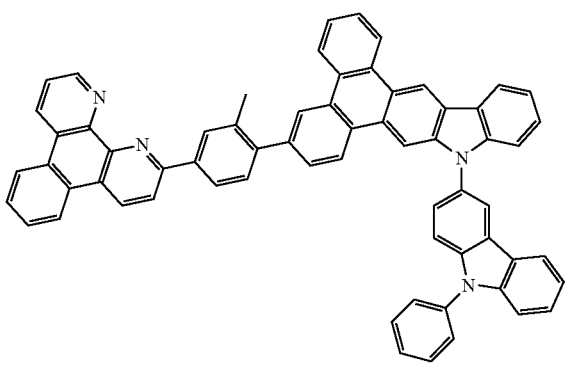
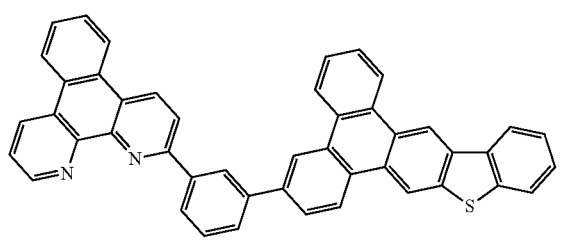
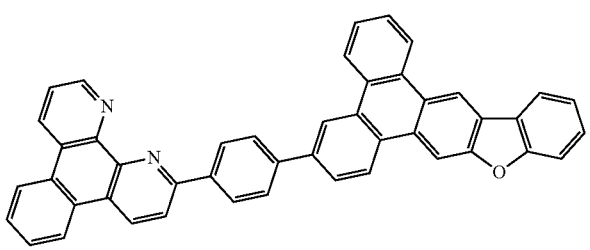
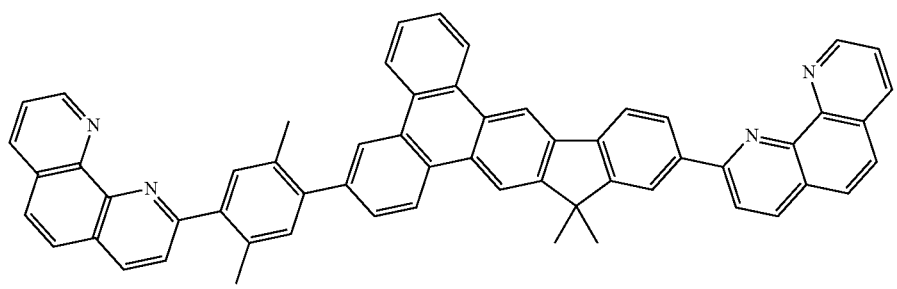
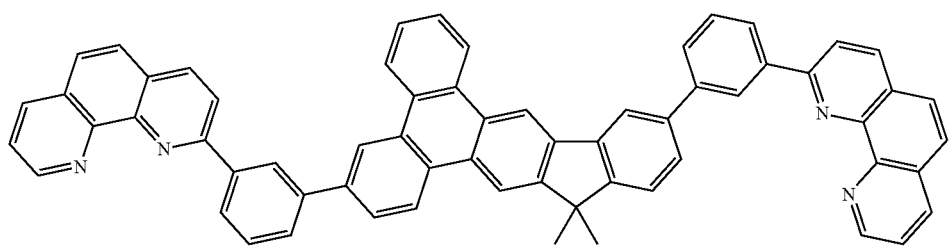
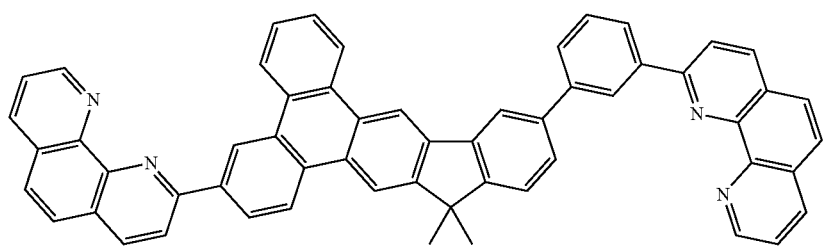

-continued
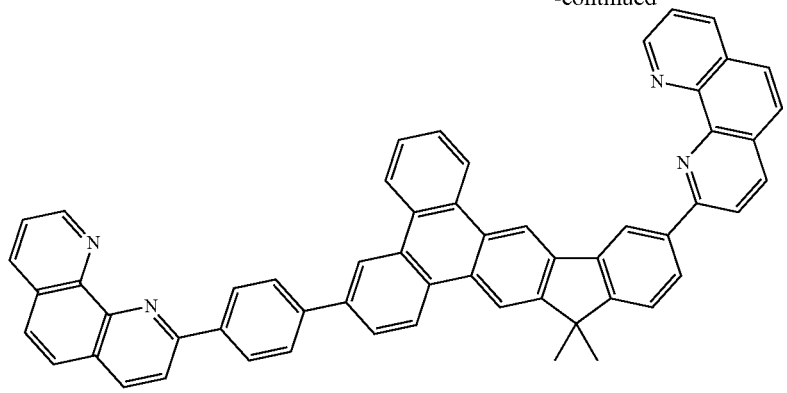
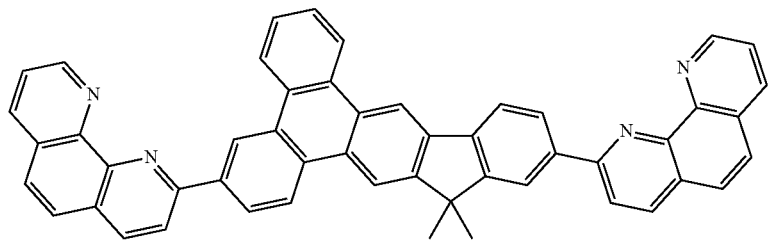
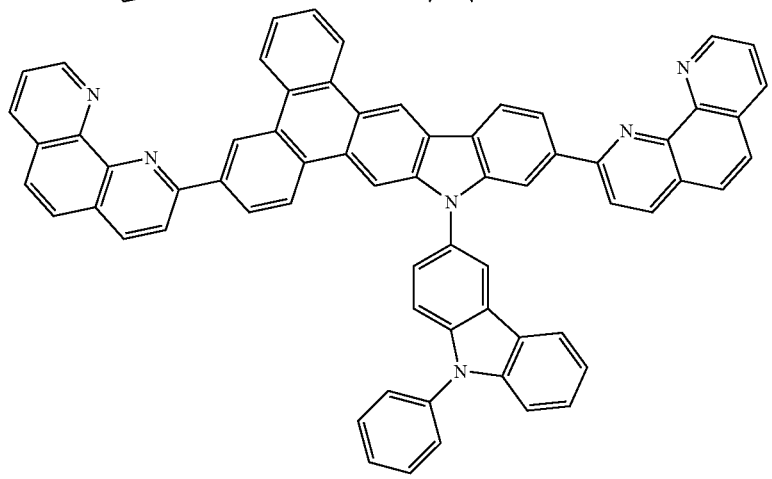
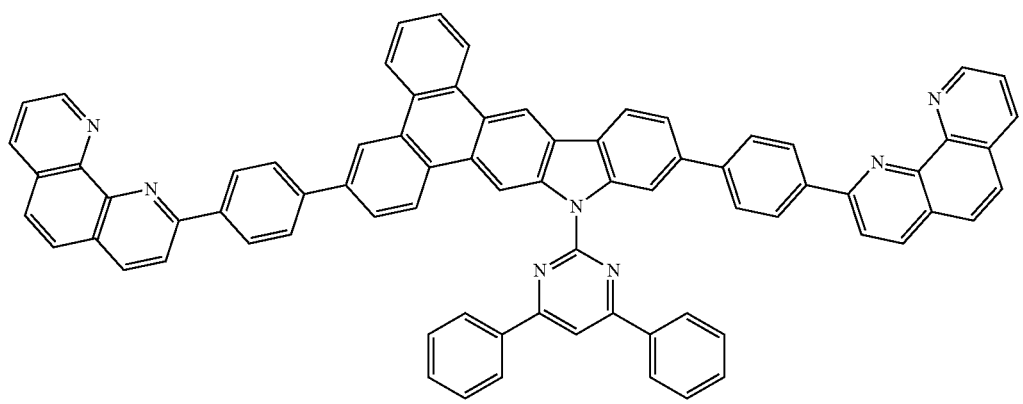

-continued
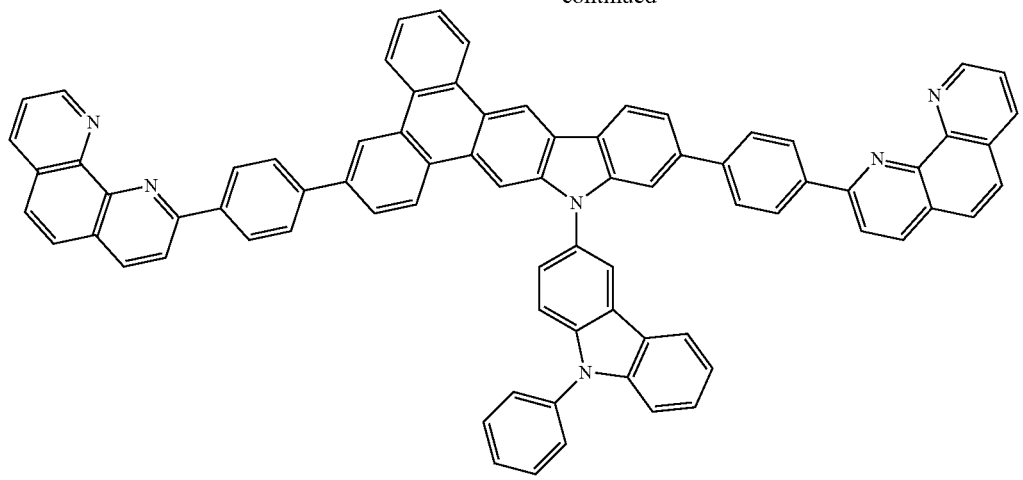
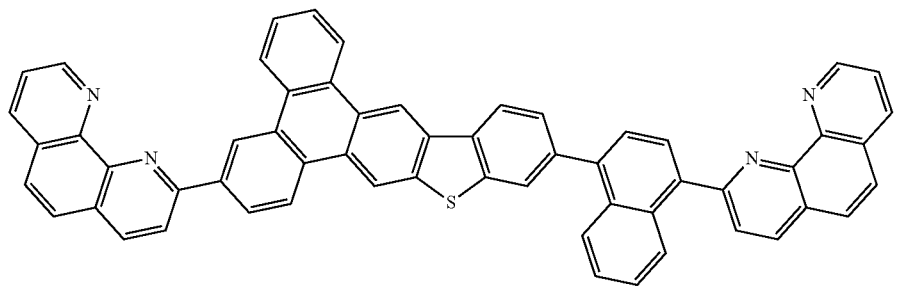
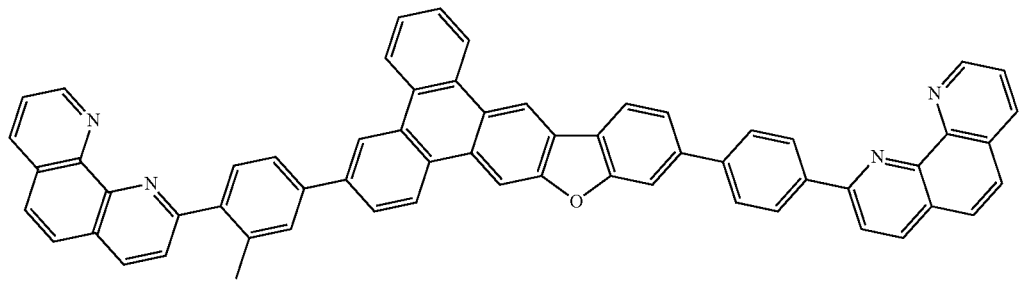
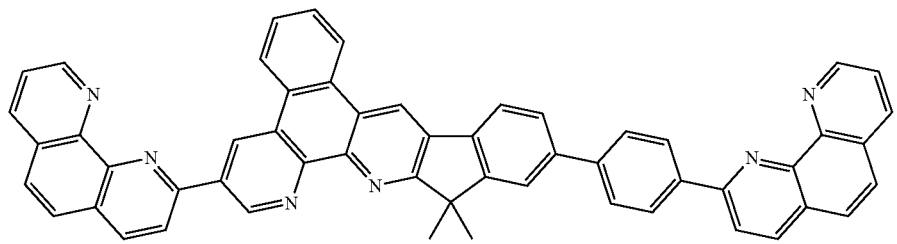
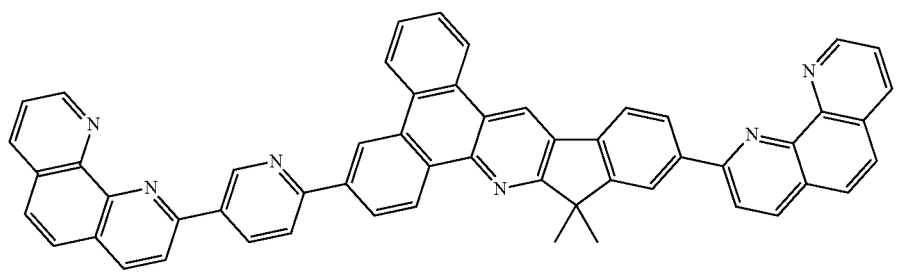

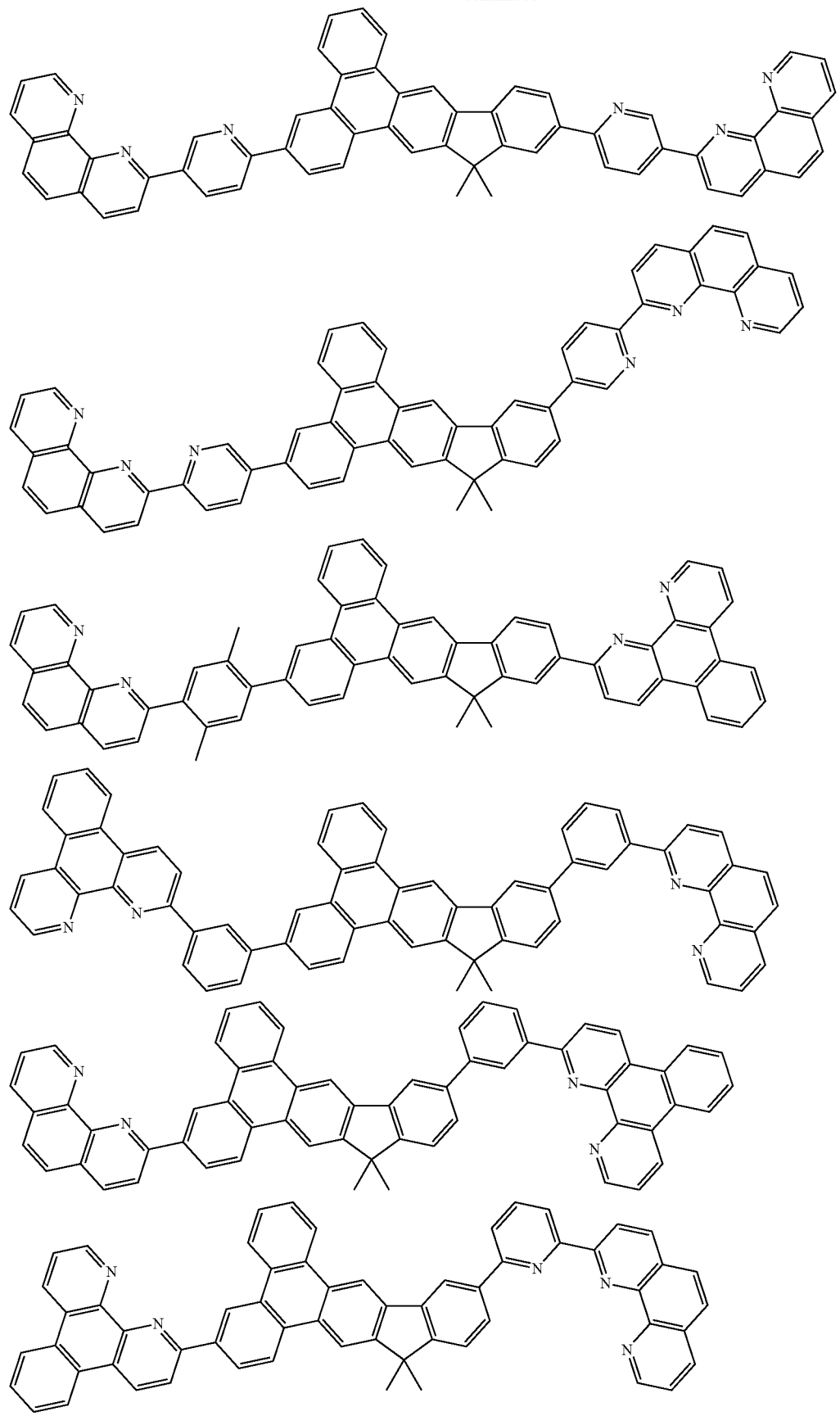

-continued
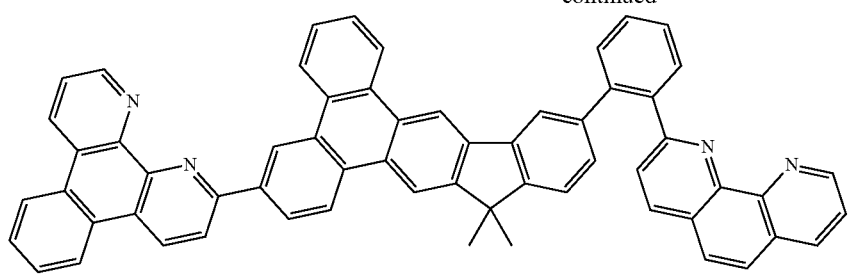
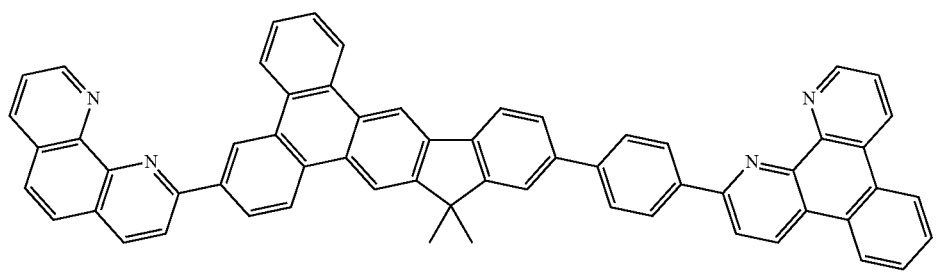
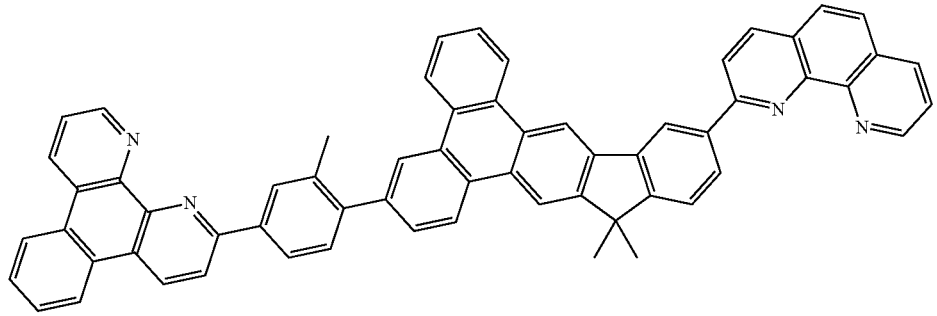
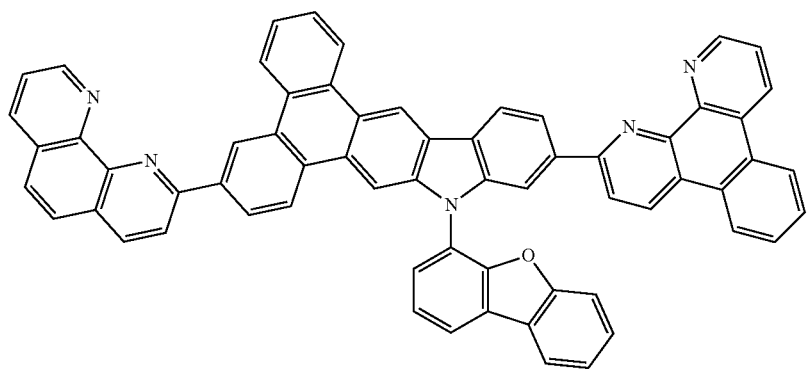
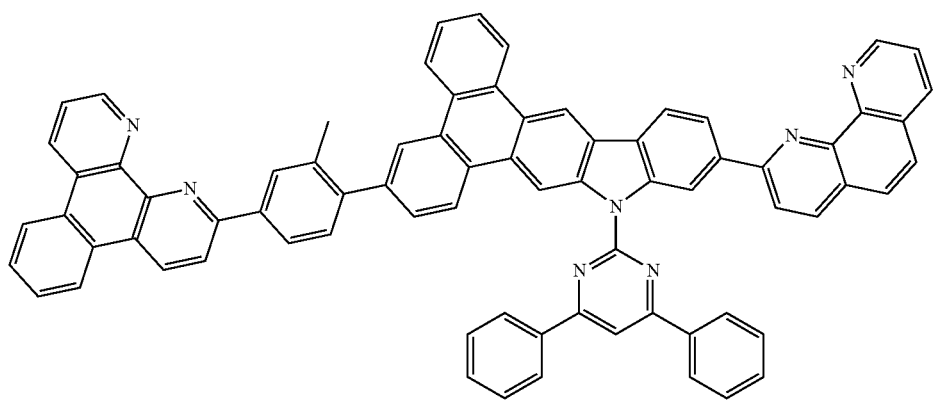

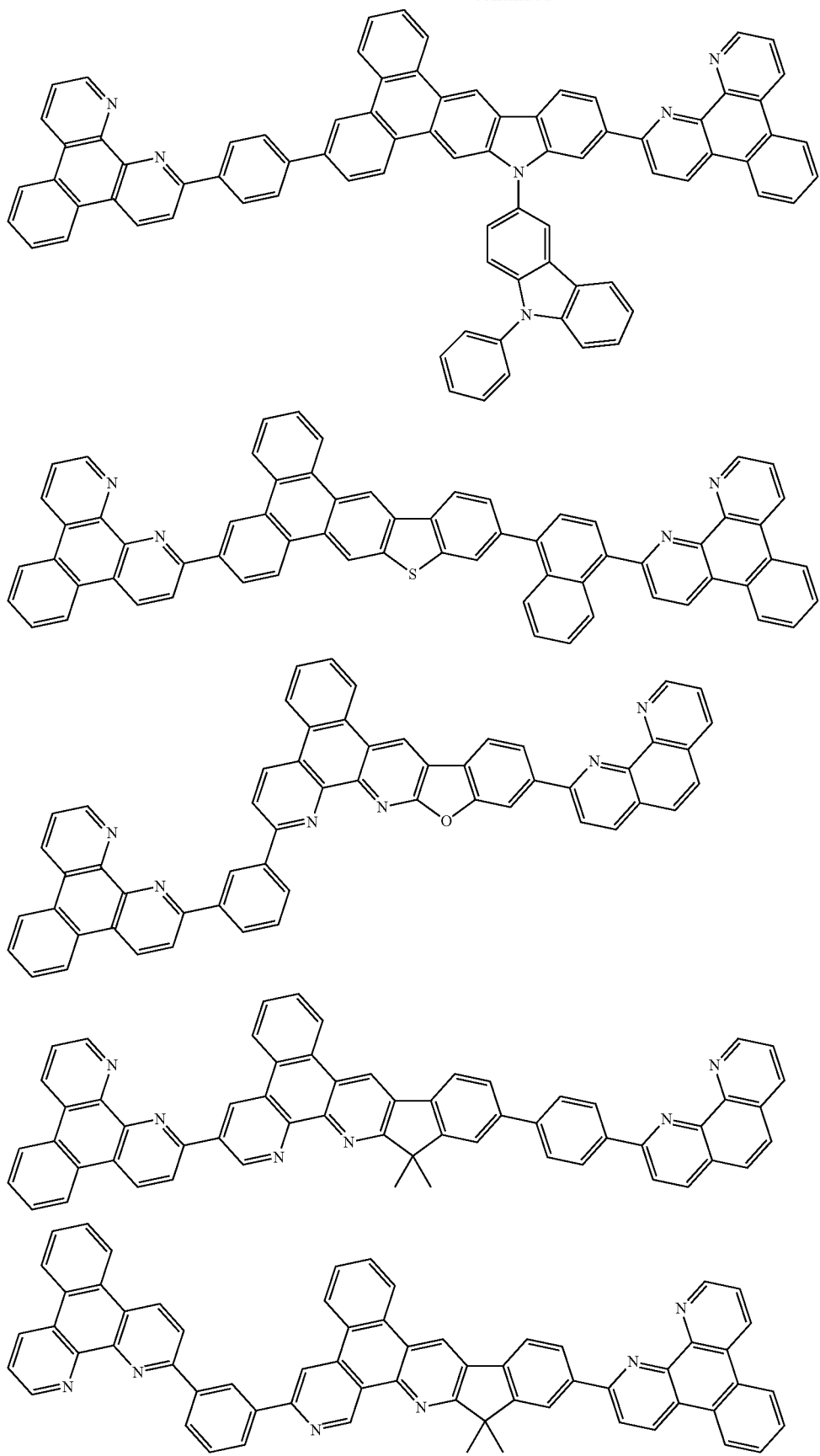

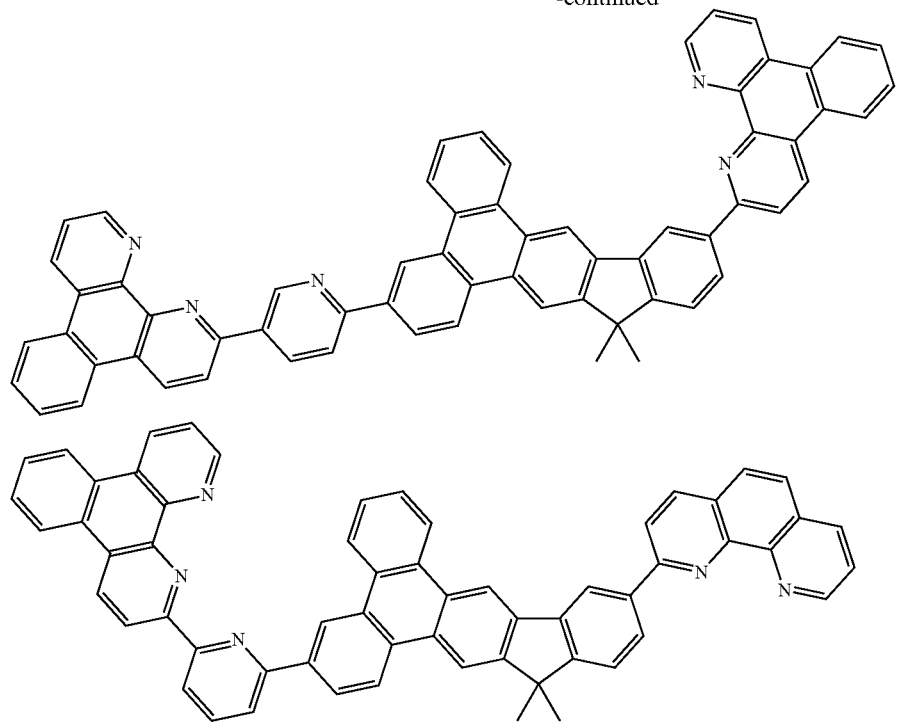

Detailed preparation for the phenanthroline-based compound in the present invention could be clarified by exemplary embodiments, but the present invention is not limited to exemplary embodiments. EXAMPLE 1~6 show the preparation for some EXAMPLES of the phenanthroline-based compound in the present invention. EXAMPLE 7 and 8 show the fabrication of organic EL device and I-V-B, half-life time of organic EL device testing report.

EXAMPLE 1

Synthesis of 2-bromo-4-methoxybiphenyl

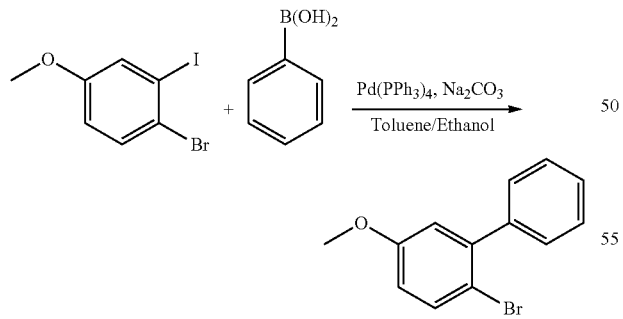

A mixture of 38 g (121 mmol) of 1-bromo-2-iodo-4-methoxy benzene, 14.8 g (121 mmol) of phenylboronic acid, 2.8 g (2.4 mmol) of tetrakis(triphenylphosphine)palladium, 2M $Na_2CO_3$ (29 g, 266 mmol), 135 ml of EtOH and 270 ml toluene was degassed and placed under nitrogen, and then heated at 90° C. for 16 h. After finishing the reaction, the mixture was allowed to cool to room temperature. The organic layer was extracted with ethyl acetate and water, dried with anhydrous magnesium sulfate, the solvent was removed and the residue was purified by column chromatography on silica(hexane-dichloromethane) to give product (24 g, 63.0 mmol, 75%).

Synthesis of 3-(4-methoxybiphenyl-2-yl)-9,9-dimethyl-9H-fluorene

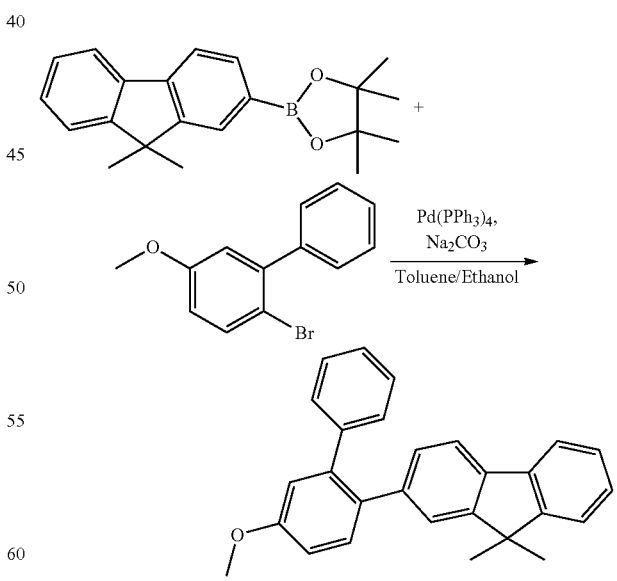

A mixture of 26.8 g (83.6 mmol) of 4,4,5,5-tetramethyl-2-(9,9-dimethyl-9H-fluoren-7-yl)-1,3,2-dioxaborolane, 20 g (76.0 mmol) of 2-bromo-4-methoxybiphenyl, 1.8 g (1.5 mmol) of tetrakis(triphenylphosphine)palladium, 2M $Na_2CO_3$ (16.1 g, 152.0 mmol), 105 ml of EtOH and 210 ml toluene was degassed and placed under nitrogen, and then heated at 90° C. for 10 h. After finishing the reaction, the mixture was allowed to cool to room temperature. The organic layer was extracted with ethyl acetate and water, dried with anhydrous magnesium sulfate, the solvent was removed and the residue was purified by column chromatography on silica(hexane-dichloromethane) to give product (20.6 g, 54.71 mmol, 72%).

Synthesis of 6-methoxy-10,10-dimethyl-10H-indeno [2,1-b]triphenylene

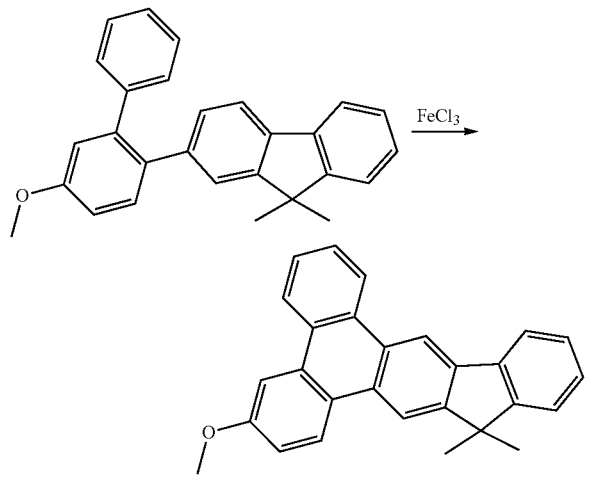

In a 100 ml three-necked flask that had been degassed and filled with nitrogen, 10 g (26.6 mmol) of 3-(4-methoxybiphenyl-2-yl)-9,9-dimethyl-9H-fluorene was dissolved in anhydrous dichloromethane (422 ml), 21.5 g (133.0 mmol) iron(III)chloride was then added, and the mixture was stirred one hour. Methanol 50 ml were added to the mixture and the organic layer was separated and the solvent was removed. The residue was purified by column chromatography on silica(hexane-dichloromethane) afforded desired product 5.47 g (14.6 mmol, 55%).

Synthesis of 10,10-dimethyl-10H-indeno[2,1-b]triphenylen-6-ol

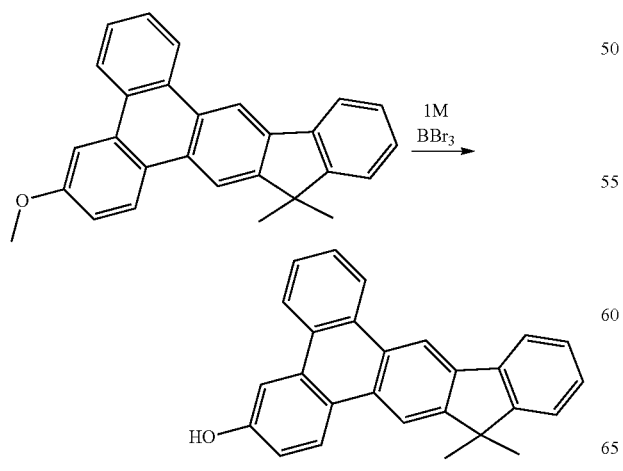

To a solution of 6-methoxy-10,10-dimethyl-10H-indeno [2,1-b]triphenylene(4.5 g, 12.0 mmol) in 250 ml dichloromethane was added 1M BBr$_3$ (24.0 ml, 24.0 mmol) at 0° C. and stirred at room temperature overnight. Then 20 ml of MeOH was added and after stirring for 10 min, it was extracted with dichloromethane and water, dried over anhydrous magnesium sulfate, the solvent was removed and the residue was purified by column chromatography on silica (hexane-dichloromethane) to give product 3.94 g (10.93 mmol, 92%).

Synthesis of 10,10-dimethyl-10H-indeno[2,1-b]triphenylen-6-yl trifluoromethanesulfonate

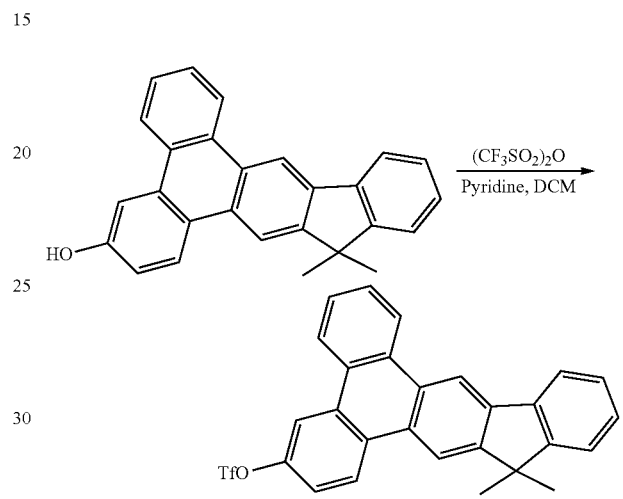

To a solution of 10,10-dimethyl-10H-indeno[2,1-b]triphenylen-6-ol (3 g, 8.3 mmol) in 90 ml dichloromethane at 0° C., pyridine (0.98 g, 12.4 mmol) was added slowly and after stirring for 10 min, 2.38 ml of trifluoromethanesulfonic anhydride (3.98 g, 14.11 mmol) was added and stirred at room temperature for overnight. When the reaction completed, water was added and extracted with dichloromethane, dried over anhydrous magnesium sulfate, the solvent was removed and the residue was purified by column chromatography on silica(hexane-dichloromethane) to give product 2.61 g (5.29 mmol, 64%).

Synthesis of 2-(10,10-dimethyl-10H-indeno[1,2-b] triphenylen-6-yl)-1,10-phenanthroline

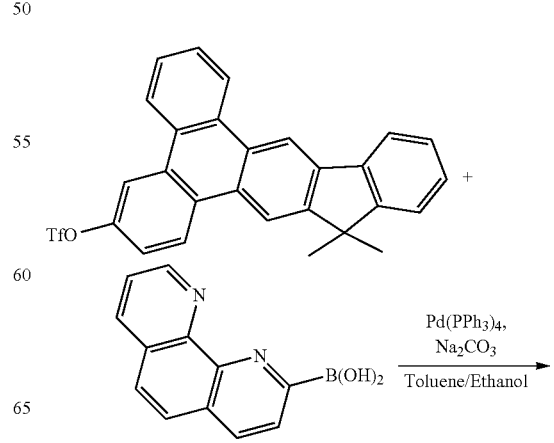

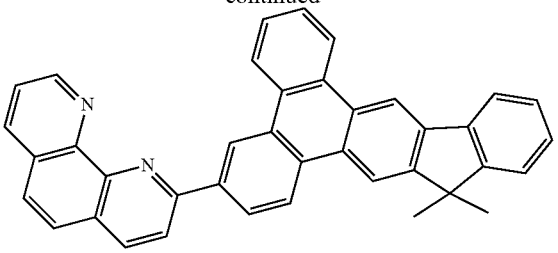

A mixture of 2.6 g (5.29 mmol) of 10,10-dimethyl-10H-indeno[2,1-b]triphenylen-6-yl-trifluoromethanesulfonate, 1.43 g (6.35 mmol) of 1,10-phenanthrolin-2-ylboronic acid, 0.25 g (0.2 mmol) of tetrakis(triphenyl phosphine)palladium, 2MNa$_2$CO$_3$ 16 ml, 20 ml of EtOH and 50 ml toluene was degassed and placed under nitrogen, and then heated at 90° C. for 16 h. After finishing the reaction, the mixture was allowed to cool to room temperature. The organic layer was extracted with ethyl acetate and water, dried with anhydrous magnesium sulfate, the solvent was removed and the residue was purified by column chromatography on silica (hexane-dichloromethane) to give product 2.2 g (79%). MS (m/z, FAB$^+$): 522.7, $^1$H NMR (CDCl$_3$, 400 MHz): chemical shift (ppm) 9.2 (s, 1H), 8.80 (d, J=8.1 Hz, 1H), 8.65~8.73 (m, 3H), 8.42~8.27 (m, 3H), 8.24~7.63 (m, 6H), 7.58~7.37 (m, 6H), 1.58 (s, 6H).

EXAMPLE 2

Synthesis of 2-(3-(4,4,5,5-tetramethyl-1,3,2-dioxaborolan-2-yl)phenyl)-1,10-phenanthroline

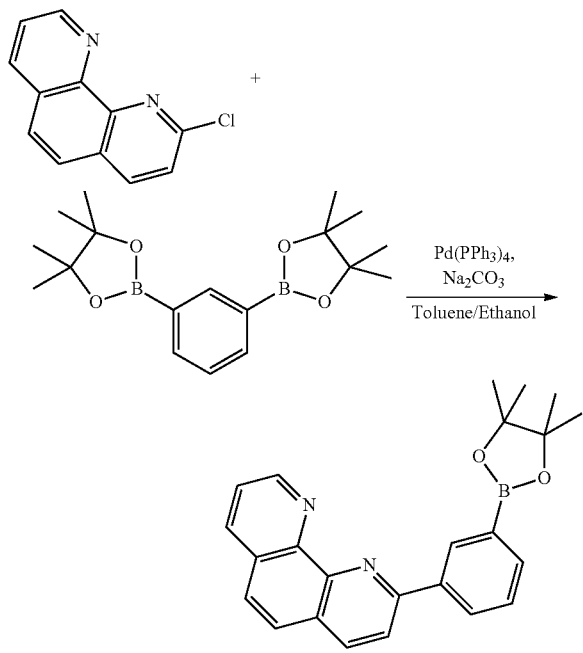

A mixture of 21.5 g (100 mmol) of 2-chloro-1,10-phenanthroline, 33 g (100 mmol) of 1,3-bis(4,4,5,5-tetramethyl-1,3,2-dioxaborolan-2-yl)benzene, 2.3 g (2 mmol) of tetrakis(triphenylphosphine)palladium, 2M Na$_2$CO$_3$ 75 ml (150 mmol), 75 ml of EtOH and 150 ml toluene was degassed and placed under nitrogen, and then heated at 90° C. for 4 h. After finishing the reaction, the mixture was allowed to cool to room temperature. The organic layer was extracted with ethyl acetate and water, dried with anhydrous magnesium sulfate, the solvent was removed and the residue was purified by column chromatography on silica (5% MeOH-dichloromethane) to give product 25.6 g (67.0 mmol, 67%).

Synthesis of 2-(3-(10,10-dimethyl-10H-indeno[1,2-b]triphenylen-6-yl)phenyl)-1,10-phenanthroline

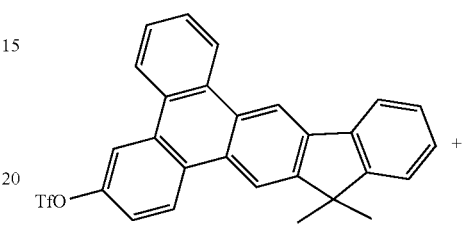

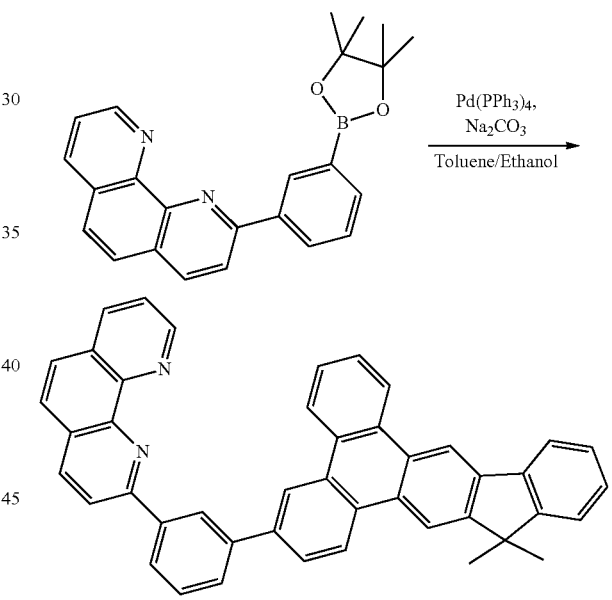

A mixture of 38.7 g (78.5 mmol) of 10,10-dimethyl-10H-indeno[2,1-b]triphenylen-6-yl-trifluoromethanesulfonate, 30 g (78.5 mmol) of 2-(3-(4,4,5,5-tetramethyl-1,3,2-dioxaborolan-2-yl)phenyl)-1,10-phenanthroline, 1.8 g (1.6 mmol) of tetrakis(triphenylphosphine)palladium, 2M Na$_2$CO$_3$ 80 ml, 100 ml of EtOH and 200 ml toluene was degassed and placed under nitrogen, and then heated at 90° C. for 16 h. After finishing the reaction, the mixture was allowed to cool to room temperature. Than 200 ml MeOH was added, while stirring and the precipitated product was filtered off with suction. To give 30 g (yield 64%) of yellow product which was recrystallized from chloroform. MS (m/z, FAB$^+$): 598.4. $^1$H NMR (CDCl$_3$, 400 MHz): chemical shift (ppm) 9.8 (s, 1H), 8.80 (d, J=8.1 Hz, 1H), 8.66~8.73 (m, 5H), 8.52~8.31 (m, 4H), 8.24~7.63 (m, 6H), 7.58~7.37 (m, 7H), 1.58 (s, 6H).

EXAMPLE 3

Synthesis of 3,6-dibromofluorene

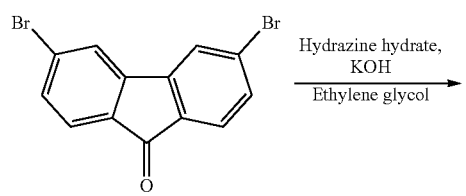

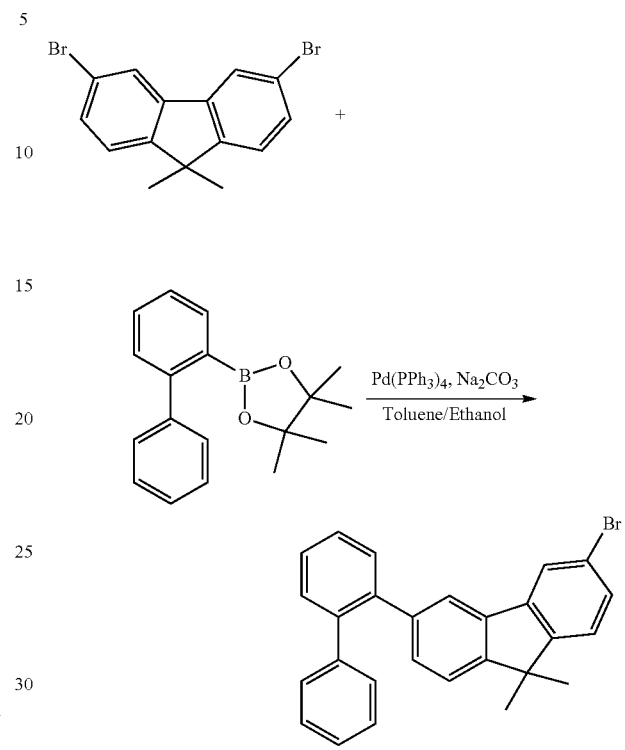

3,6-Dibromo-9-fluorenone (4 g, 11.83 mmol) was dispersed in 175 ml of ethylene glycol and hydrazine hydrate (80%, 21.8 ml, 63.88 mmol) was added. While stirring overnight at 100° C. The solution slowly turned clear. Then, KOH (3.36 g in 10 mL of water) was added. Stirring was continued for 2 h at 130° C. After cooling to room temperature, the mixture was poured into 1500 ml of water and neutralized with HCl. The orange precipitate was filtered off, dried and was purified by column chromatography on silica (hexane-ethyl acetate) to give 3,6-dibromofluorene (2.56 g, 7.9 mmol, 67% yield) was obtained as a nearly white solid. $^1$H NMR (400 MHz, CDCl$_3$) chemical shift (ppm) 7.84 (s, 2H), 7.44 (dd, J=8.0, 1.5 Hz, 2H), 7.40 (s, 2H), 3.80 (s, 2H).

Synthesis of 3,6-Dibromo-9,9-dimethylfluorene

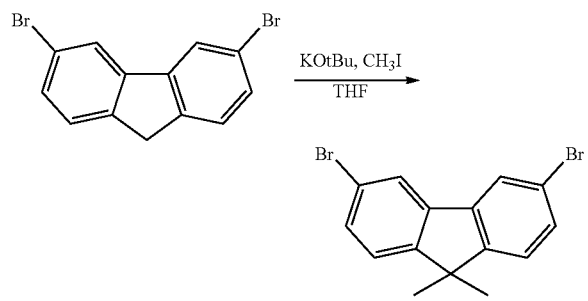

3,6-Dibromofluorene (2.56 g, 7.9 mmol) was dissolved in dry THF (150 ml) and cooled to 0° C. KOtBu (2.65 g, 23.7 mmol) was added, and after stirring for 10 min, CH$_3$I (1.4 ml, 23.7 mmol) was added. The solution was allowed to warm to room temperature and it was stirred overnight. Then water was added and the mixture was extracted with ethyl acetate, column chromatography (cyclohexane) gave 2.56 g (7.27 mmol, 92% yield) 3,6-dibromo-9,9-dimethylfluorene as a white solid. $^1$H NMR (CDCl$_3$, 400 MHz): chemical shift (ppm) 7.78 (s, 2H), 7.42 (d, J=8.0, 2H), 7.27 (d, J=8.0 Hz, 2H), 1.43 (s, 6H).

Synthesis of 3-(biphenyl-2-yl)-6-bromo-9,9-dimethyl-9H-fluorene

A mixture of 2.56 g (7.27 mmol) of 3,6-dibromo-9,9-dimethyl fluorene, 1.38 g (7.27 mmol) of biphenyl-2-ylboronic acid, 0.16 g (0.15 mmol) of tetrakis(triphenylphosphine)palladium, 0.09 g 2-(dicyclohexylphosphino)biphenyl(0.29 mmol), 7 ml of 2M Na$_2$CO$_3$, 20 ml of EtOH and 40 ml toluene was degassed and placed under nitrogen, and then heated at 100° C. for 16 hours. After finishing the reaction, the mixture was allowed to cool to room temperature. The organic layer was extracted with ethyl acetate and water, dried with anhydrous magnesium sulfate, the solvent was removed and the residue was purified by column chromatography on silica (hexane-dichloromethane) to give product (1.7 g, 63.0 mmol, 55%) as a white solid. $^1$H NMR (CDCl$_3$, 400 MHz): chemical shift (ppm) 7.61 (d, J=1.7 Hz, 1H), 7.59~7.45 (m, 7H), 7.36~7.22 (m, 6H), 7.10 (dd, J=1.5, 1.5 Hz, 1H), 1.49 (s, 6H).

Synthesis of 13-bromo-10,10-dimethyl-10H-indeno[2,1-b]triphenylene

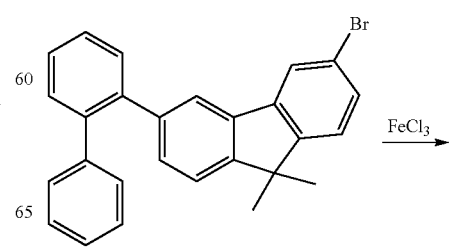

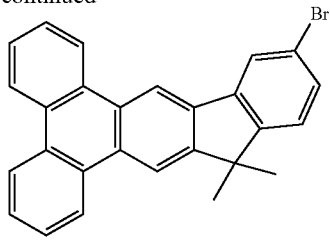

In a 100 ml three-necked flask that had been degassed and filled with nitrogen, 1.7 g (3.99 mmol) of 2-(biphenyl-2-yl)-6-bromo-9,9-dimethyl-9H-fluorene was dissolved in anhydrous dichloromethane (80 ml), 3.24 g (20.0 mmol) iron(III)chloride was then added, and the mixture was stirred one hour. Methanol 30 ml were added to the mixture and the organic layer was separated and the solvent was removed. The residue was purified by column chromatography on silica(hexane-dichloromethane) afforded a white solid (0.67 g, 1.58 mmol, 39%). $^1$H NMR (CDCl$_3$, 400 MHz): chemical shift (ppm) (1H), 8.77~8.71 (m, 2H), 8.66~8.64 (m, 3H), 8.08 (d, J=1.5 Hz, 1H), 7.70~7.63 (m, 4H), 7.48 (dd, J=8.0, 1.7 Hz, 1H), 7.36 (d, J=8.5 Hz, 1H), 1.62 (s, 6H).

Synthesis of 1-methylbenzo[f][1,10]phenanthrolin-1-ium iodide

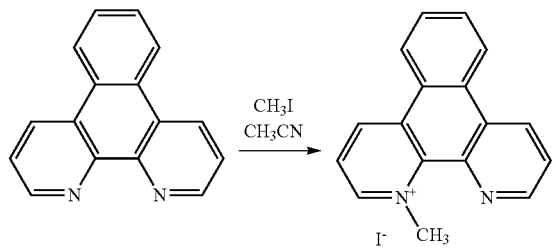 [SMILES: c1ccc2c(c1)c1cccnc1c1ncccc21 ; C[n+]1cccc2c3ccccc3c3cccnc3c21 ; [I-]]

The benzo[f][1,10]phenanthroline 23.0 g (100 mmol) was added to round bottom flask followed by dry acetonitrile (200 ml). Methyl iodide 42.6 g (300 mmol) was added to the stirring solution, which was then heated to reflux for 3 hours. The solution was cooled to room temperature and the yellow precipitate was collected by filtration to give 33.8 g (yield 91%) of product.

Synthesis of 1-methylbenzo[f][1,10]phenanthrolin-2(1H)-one

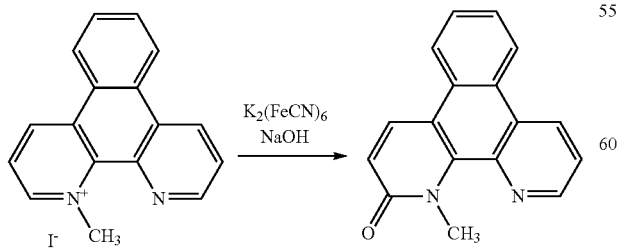

NaOH (40 g, 1 mol) was added slowly with stirring to an aqueous solution of [K$_3$Fe(CN)$_6$](123 g, 374 mmol in 300 ml water). The flask was placed in an ice/water bath and cooled to 2~5° C. 1-methylbenzo[f][1,10]phenanthrolin-1-ium iodide (14 g, 37.4 mmol) was dissolved in water (140 ml) and added dropwise to the flask maintaining the temperature at 2~5° C. The reaction mixture was allowed to stir for 6 h, before it was neutralized to pH 7~8 with 4MHCl. The beige brown solid was partially dissolved in CHCl$_3$ and left to stir overnight, then filtered, concentrated and dried under vacuum. The residue was purified by column chromatography on silica (5% methanol-dichloromethane) to give product 7.9 g (yield 81%) as a light-yellow solid.

Synthesis of 2-chlorobenzo[f][1,10]phenanthroline

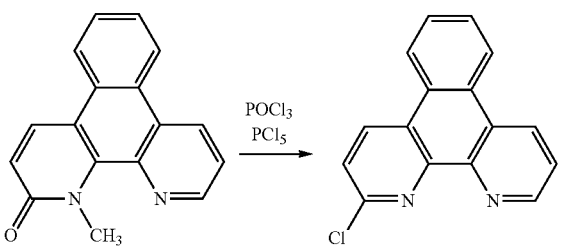 [SMILES: Cn1c(=O)ccc2c3ccccc3c3cccnc3c21 ; Clc1ccc2c3ccccc3c3cccnc3c2n1]

1-Methylbenzo[f][1,10]phenanthrolin-2(1H)-one 7.9 g (30.3 mmol) was dissolved in 30 ml POCl$_3$ and PCl$_5$ 12.6 g (60.7 mmol) was added. The mixture was degassed and refluxed at 110° C. overnight. Excess POCl$_3$ was removed by distillation and the solid material was decomposed with ice. The suspension was neutralized with ammonia solution (30%, aqueous) with cooling. The organic layer was extracted with CH$_2$Cl$_2$ and water, dried with anhydrous magnesium sulfate, the solvent was removed and the residue was purified by column chromatography on silica(hexane-dichloromethane) to give product (5.7 g, 18.4 mmol, 71%)

Synthesis of 2-(10,10-dimethyl-10H-indeno[2,1-b]triphenylen-13-yl)-4,4,5,5-tetramethyl-1,3,2-dioxaborolane

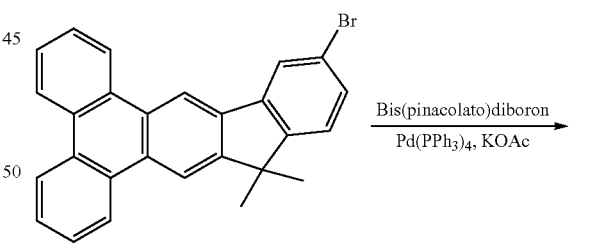

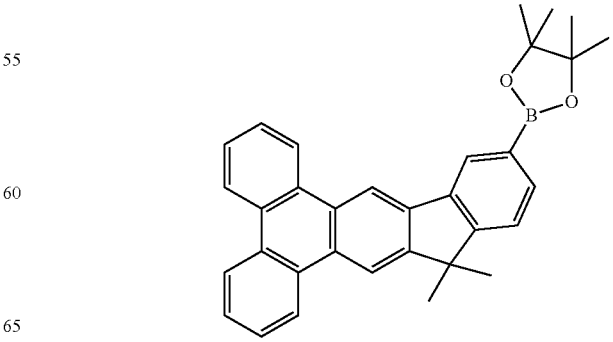

A mixture of 10.g (25.3 mmol) of 13-bromo-10,10-dimethyl-10H-indeno[2,1-b]triphenylene, 7.7 g (30.3 mmol) of bis(pinacolato)diboron, 0.3 g (0.26 mmol) of tetrakis(triphenylphosphine)palladium, 7.4 g (75.4 mmol) of potassium acetate, and 300 ml 1,4 dioxane was degassed and placed under nitrogen, and then heated at 90° C. for 16 h. After finishing the reaction, The mixture was allowed to cool to room temperature. The organic phase separated and washed with ethyl acetate and water. After drying over magnesium sulfate, the solvent was removed in vacuo. The residue was purified by column chromatography on silica(hexane-dichloromethane) to give product (9.5 g, 20.2 mmol, 80%) as a light-yellow solid.

Synthesis of 2-(10,10-dimethyl-10H-indeno[1,2-b]triphenylen-13-yl)benzo[f][1,10]phenanthroline

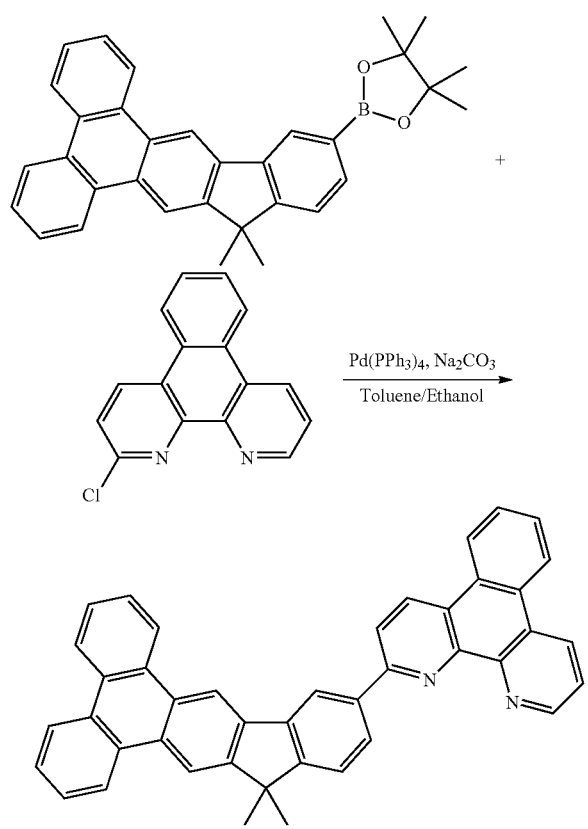

A mixture of 8.6 g (18.4 mmol) of 2-(10,10-dimethyl-10H-indeno[1,2-b]triphenylen-13-yl)-4,4,5,5-tetramethyl-1,3,2-dioxaborolane, 5.7 g (18.4 mmol) of 2-chlorobenzo[f][1,10]phenanthroline, 0.45 g (0.4 mmol) of tetrakis(triphenylphosphine)palladium, 18 ml of 2M Na$_2$CO$_3$, 25 ml of EtOH and 50 ml toluene was degassed and placed under nitrogen, and then heated at 90° C. for 24 h. After finishing the reaction, The mixture was allowed to cool to room temperature. Than 100 ml MeOH was added, while stirring and the precipitated product was filtered off with suction. To give 7.6 g (yield 72%) of yellow product which was recrystallized from chloroform. MS (m/z, EI): 572.9.

$^1$H NMR (CDCl$_3$, 400 MHz): chemical shift (ppm) (d, J=8.1 Hz, 1H), 8.65~8.73 (m, 3H), 8.42~8.27 (m, 4H), 8.24~7.63 (m, 7H), 7.58~7.37 (m, 6H), 1.58 (s, 6H).

EXAMPLE 4

Synthesis of 3',6'-dibromo-9-phenyl-9H-3,9'-bicarbazole

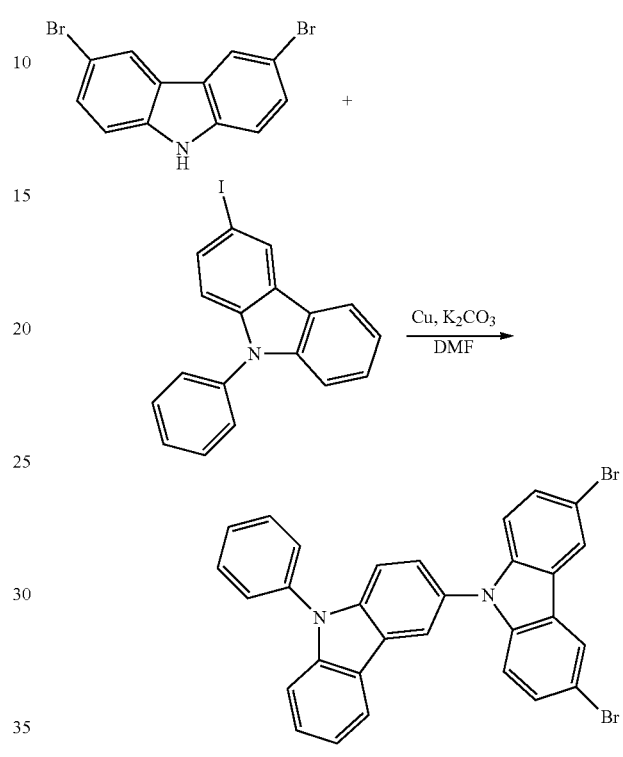

A mixture of 32.5 g (100 mmole) 3,6-dibromo-9H-carbazole, 36.9 g (100 mmole) 3-iodo-9-phenyl-9H-carbazole, 9.5 g (150 mmole) of copper powder, 27.6 g (200 mmole) of potassium carbonate, and 600 ml dimethylformamide were heated at 130° C. under nitrogen overnight, then cooled to room temperature, the solution was filtered. The filtrate was extracted three times with dichloromethane and water, dried with anhydrous magnesium sulfate, the solvent was evaporated in vacuum. The residue was purified by column chromatography on silica(hexane-dichloromethane) afforded a white solid (34.5 g, 61 mmol, 61%)

Synthesis of 3'-(biphenyl-2-yl)-6'-bromo-9-phenyl-9H-3,9'-bicarbazole

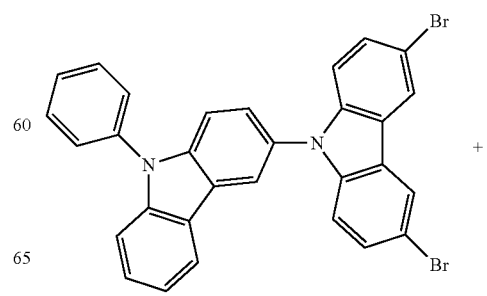

-continued

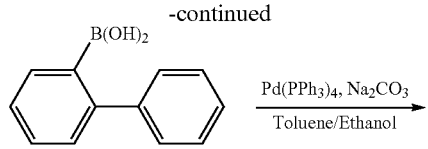

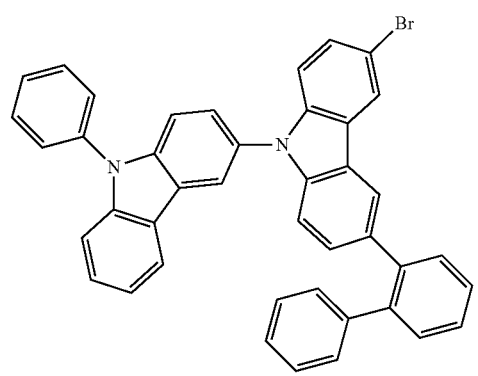

A mixture of 16.7 g (29.6 mmol) 3',6'-dibromo-9-phenyl-9H-3,9'-bicarbazole, 5.9 g (29.6 mmol) of biphenyl-2-ylboronic acid, 0.7 g (0.6 mmol) of tetrakis(triphenylphosphine) palladium, 30 ml of 2M Na$_2$CO$_3$, 60 ml of EtOH and 150 ml toluene was degassed and placed under nitrogen, and then heated at 110° C. for 16 h. After finishing the reaction, the mixture was allowed to cool to room temperature. The reaction mixture was extracted with toluene and water, dried with anhydrous magnesium sulfate, the solvent was evaporated in vacuum. The residue was purified by column chromatography on silica (hexane-dichloromethane) afforded a white solid 9.1 g (48%).

Synthesis of 13-bromo-10-(9-phenyl-9H-carbazol-3-yl)-10H-phenanthro[9,10-b]carbazole In a 2000 ml three-necked flask that had been deaerated and filled with nitrogen, 7.5 g (11.7 mmol) of 3'-(biphenyl-2-yl)-6'-bromo-9-phenyl-9H-3,9'-bicarbazole was dissolved in anhydrous dichloromethane (900 ml), 38 g (234 mmol) iron(III)chloride was then added, and the mixture was stirred one hour. Methanol 300 ml were added to the mixture and the organic layer was separated and the solvent removed in vacuum. The residue was purified by column chromatography on silica(hexane-dichloromethane) afforded a white solid (5.3 g, 71%)

Synthesis of 13-(1,10-phenanthrolin-2-yl)-10-(9-phenyl-9H-carbazol-3-yl)-10H-phenanthro[9,10-b]carbazole

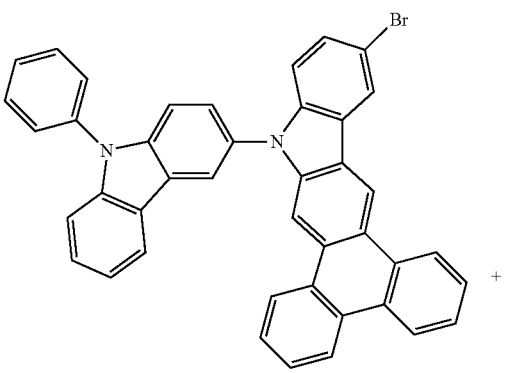

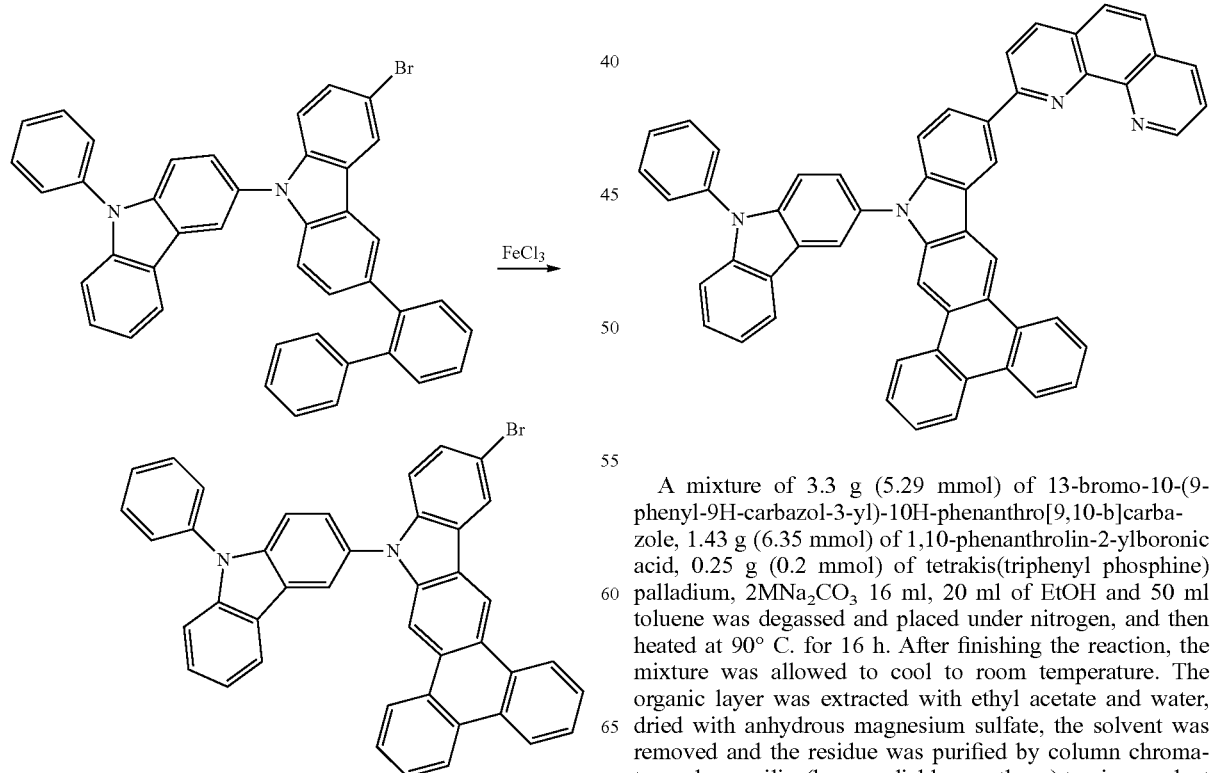

A mixture of 3.3 g (5.29 mmol) of 13-bromo-10-(9-phenyl-9H-carbazol-3-yl)-10H-phenanthro[9,10-b]carbazole, 1.43 g (6.35 mmol) of 1,10-phenanthrolin-2-ylboronic acid, 0.25 g (0.2 mmol) of tetrakis(triphenyl phosphine) palladium, 2MNa$_2$CO$_3$ 16 ml, 20 ml of EtOH and 50 ml toluene was degassed and placed under nitrogen, and then heated at 90° C. for 16 h. After finishing the reaction, the mixture was allowed to cool to room temperature. The organic layer was extracted with ethyl acetate and water, dried with anhydrous magnesium sulfate, the solvent was removed and the residue was purified by column chromatography on silica(hexane-dichloromethane) to give product 2.7 g (71%). MS (m/z, FAB+): 736.1, ¹H NMR (CDCl₃, 400 MHz): chemical shift (ppm) 9.13 (d, J=7.8 Hz 1H), 8.61~8.41 (m, 4H), 8.18~8.01 (m, 9H), 7.81~7.53 (m, 10H), 7.3~57.01 (m, 7H), 6.74 (d, J=8.0 Hz 1H).

EXAMPLE 5

Synthesis of benzo[f][1,10]phenanthroline

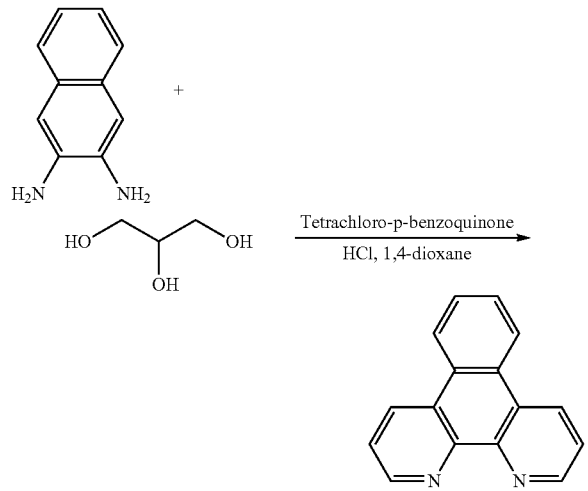

A mixture of 10 g (63.2 mmol) of naphthalene-2,3-diamine, 12.8 g (139.0 mmol) of glycerol, 17 g (69.5 mmol) of tetrachloro-p-benzoquinone and 300 ml HCl was refluxed at 90° C. for 24 hours. After cooled to 60° C., the upper layer of the precipitate was decanted off and after cooling at room temperature, to the combined residual 30% NaOH was added to make the pH10~11 and kept for standing overnight. After draining the water, the solid precipitate was dissolved in dichloromethane and 30% NaOH was added to make the pH 10~11. After extraction and evaporation, the solid was rinsed with acetone resulting a solid. After drying, the solid was sequentially dissolved in 1,4-dioxane and refluxed. Then it was cooled to precipitate overnight, with acetone washed and the desired product was obtained (2.76 g, 19%).

Synthesis of 6,7-dihydro-5H-benzo[f][1,4]diazepino[1,2,3,4-lmn][1,10]phenanthroline-4,8-diium

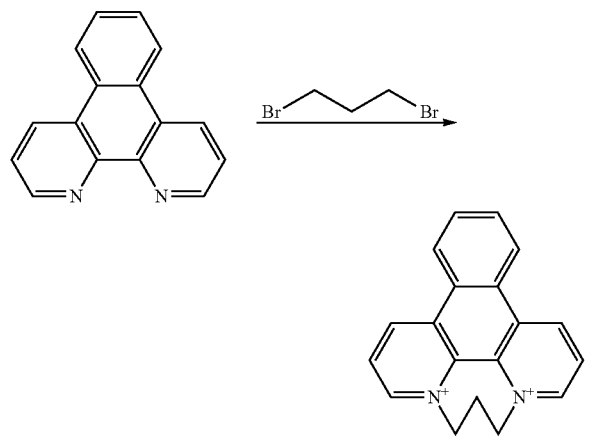

To a solution of benzo[f][1,10]phenanthroline (10.00 g, 43.4 mmol) dissolved in nitrobenzene (80 ml), 1,3-dibromopropane (33 ml) was added dropwise. The mixture was refluxed at 120° C. for 16 h. After finishing the reaction, the mixture was allowed to cool to room temperature. The crystals were collected by filtration and dried under vacuum for 8 hours. The crystals were dissolved in 80 ml water and warmed to 80° C. Ethanol 160 ml was added slowly, while stirring and the precipitated product was filtered off with suction to give 10.2 g (yield 86%) of white product.

Synthesis of 6,7-dihydro-3H-benzo[f][1,4]diazepino[1,2,3,4-lmn][1,10]phenanthroline-3,9 (5H)-dione

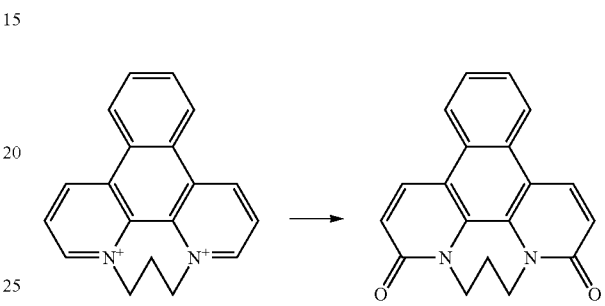

NaOH (40 g, 1 mol) was added slowly with stirring to an aqueous solution of [K₃Fe(CN)₆] (123 g, 374 mmol in 300 ml water). The flask was placed in an ice/water bath and cooled to 2~5° C. 6,7-Dihydro-5H-benzo[f][1,4]diazepino[1,2,3,4-lmn][1,10]phenanthroline-4,8-diium (10.2 g, 37.4 mmol) was dissolved in water (50 ml) and added dropwise to the flask maintaining the temperature at 2~5° C. The reaction mixture was allowed to stir for 6 h, before it was neutralized to pH 7~8 with 4MHCl. The beige brown solid was partially dissolved in CHCl₃ and left to stir overnight, then filtered, concentrated and dried under vacuum. The residue was purified by column chromatography on silica (5% methanol-dichloromethane) to give product 8.8 g (yield 78%) as a light-yellow solid.

Synthesis of 2,11-dichlorobenzo[f][1,10]phenanthroline

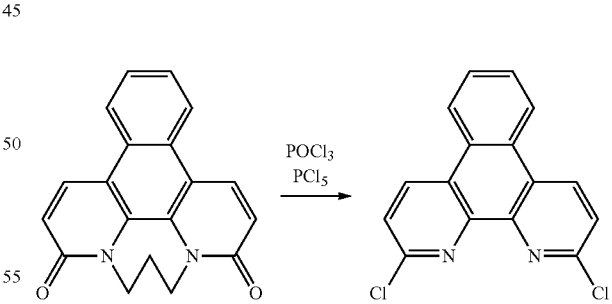

6,7-Dihydro-3H-benzo[f][1,4]diazepino[1,2,3,4-lmn][1,10]phenanthroline-3,9(5H)-dione (8.8 g, 29.1 mmol) was dissolved in POCl₃ (72 ml) and PCl₅ (12.1 g, 58.2 mmol) was added. The mixture was degassed and refluxed at 110° C. overnight. Excess POCl₃ was removed by distillation and the solid material was decomposed with ice. The suspension was neutralized with ammonia solution (30%, aqueous) with cooling. The organic layer was extracted with CH₂Cl₂ and water, dried with anhydrous magnesium sulfate, the solvent was removed and the residue was purified by column chromatography on silica(hexane-dichloromethane) to give product (5.5 g, 18.4 mmol, 63%)

Synthesis of 2-chloro-11-phenylbenzo[f][1,10]phenanthroline

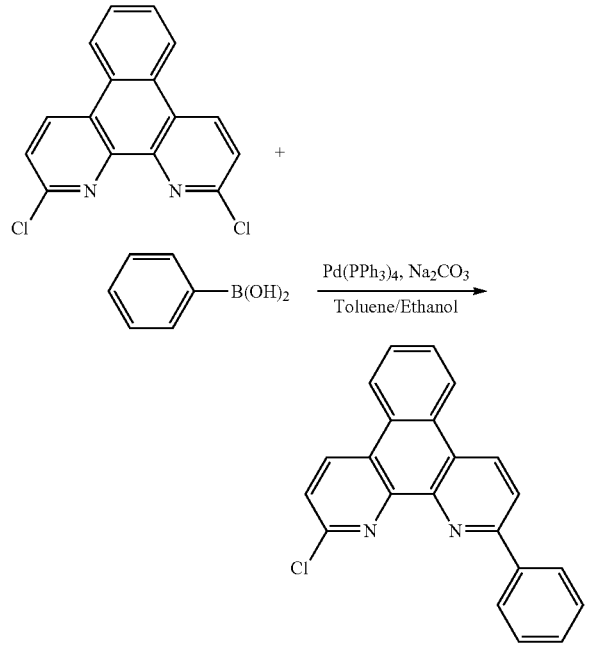

A mixture of 5.5 g (18.4 mmol) of 2,11-dichlorobenzo[f][1,10]phenanthroline, 2.47 g (20 mmol) of phenylboronic acid, 0.4 g (0.4 mmol) of tetrakis(triphenylphosphine)palladium, 27 ml of 2M Na₂CO₃, 40 ml of EtOH and 100 ml toluene was degassed and placed under nitrogen, and then heated at 90° C. for 12 h. After finishing the reaction, the mixture was allowed to cool to room temperature. Than 500 ml MeOH was added, while stirring and the precipitated product was filtered off with suction and the residue was purified by column chromatography on silica(hexane-dichloromethane) to give product 3.4 g (53%) as a white solid.

Synthesis of 1,3-bis(11-phenylbenzo[f][1,10]phenanthrolin-2-yl)benzene

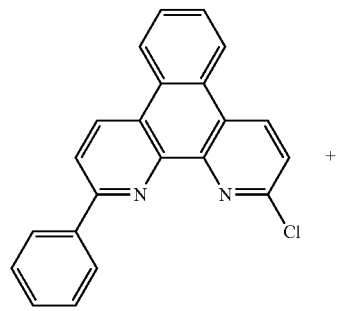

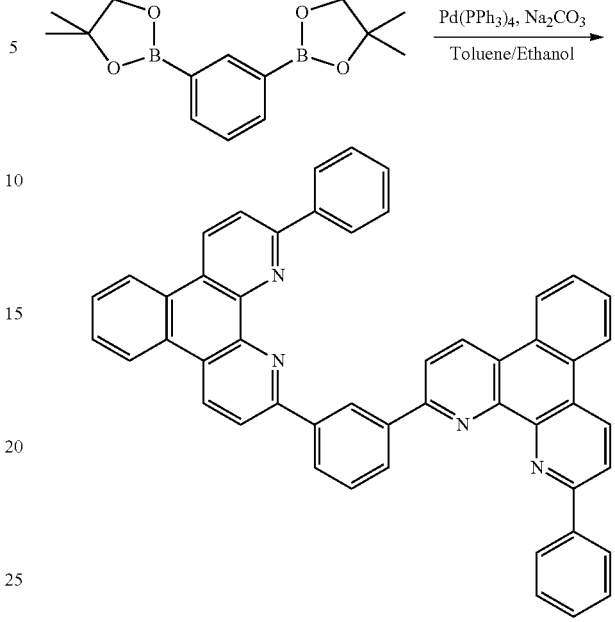

A mixture of 3.4 g (10 mmol) of 2-chloro-11-phenylbenzo[f][1,10]phenanthroline, 1.65 (5 mmol) of 1,3-bis(4,4,5,5-tetramethyl-1,3,2-dioxaborolan-2-yl)benzene, 0.23 g (0.2 mmol) of tetrakis(triphenylphosphine)palladium, 22 ml of 2MNa₂CO₃, 60 ml of EtOH and 130 ml toluene was degassed and placed under nitrogen, and then heated at 90° C. overnight. After finishing the reaction, the mixture was allowed to cool to room temperature. The precipitated product was filtered off with suction to give 3.5 g (yield 61%) of yellow product which was recrystallized from chloroform. MS (m/z, FAB⁺): 687.5.

EXAMPLE 6

Synthesis of benzo[f][1,10]phenanthroline

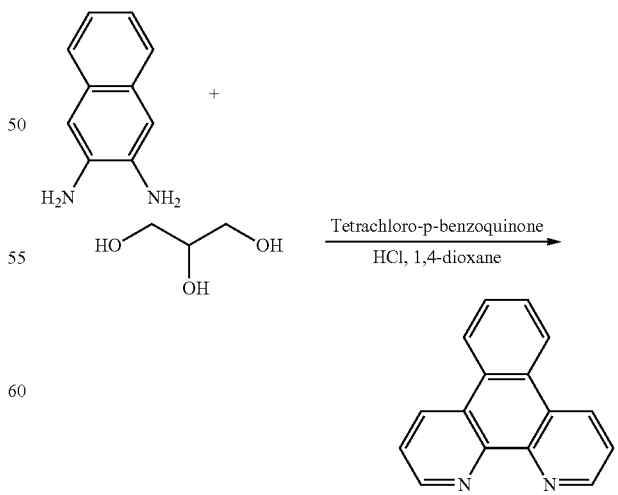

A mixture of 10 g (63.2 mmol) of naphthalene-2,3-diamine, 12.8 g (139.0 mol) of glycerol, 17 g (69.5 mmol)

of tetrachloro-p-benzoquinone and 300 ml HCl was refluxed at 90° C. for 24 hours. At 60° C., the upper layer of the precipitate was decanted off and after cooling at room temperature, to the combined residual 30% NaOH was added to make the pH10~11 and kept for standing for overnight. After draining the water, the solid precipitate was dissolved in dichloromethane and 30% NaOH was added to make the pH10~11. After extraction and evaporation, the solid was rinsed with acetone resulting a solid. After drying, the solid was sequentially dissolved in 1,4-dioxane and refluxed. Then it was cooled to precipitate for overnight, with acetone wash to get the desired product 2.76 g (19%).

Synthesis of 3-bromobenzo[f][1,10]phenanthroline

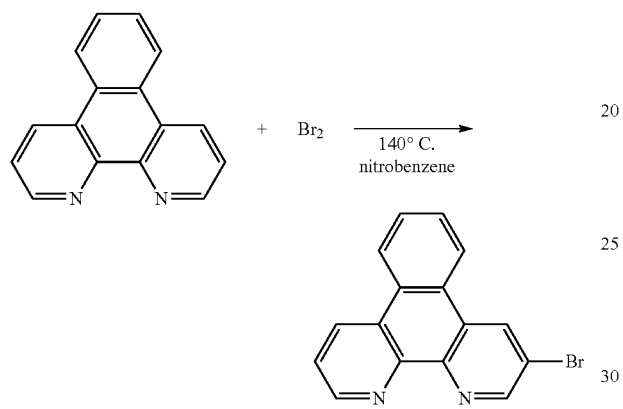

The 80 mL of nitrobenzene were added to benzo[f][1,10]phenanthroline 23 g (100 mmol) into a two necked flask and heated at 140° C. Then a solution of bromine 8.25 mL (160 mmol) in 30 mL of nitrobenzene was added drop wise to the flask. The total amount of the bromine was added over a period of one hour. The mixture was left for 8 hours at 140° C. and the mixture was cooled to room temperature. The precipitate was filtered and 100 mL of 25% aqueous NH$_4$OH were added to the filtrate. The solution was extracted three times with 100 mL of CH$_2$Cl$_2$. The organic layer was dried with anhydrous magnesium sulfate and the solvent was evaporated under reduced pressure. The residue was purified by column chromatography on silica (MeOH~CH$_2$Cl$_2$) to give product 11.7 (38%).

Synthesis of 3-(3-(4,4,5,5-tetramethyl-1,3,2-dioxaborolan-2-yl)phenyl)benzo[f][1,10]phenanthroline

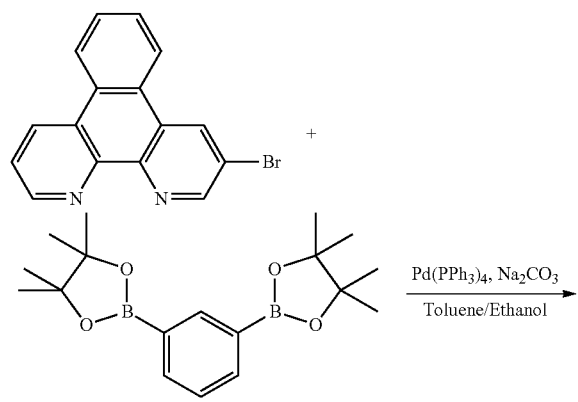

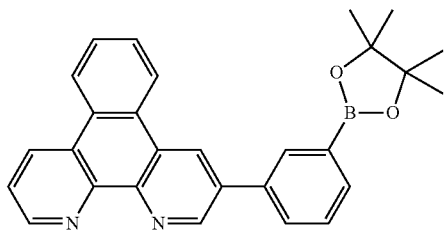

A mixture of 6.2 g (20 mmol) of 3-bromobenzo[f][1,10]phenanthroline, 6.6 (20 mmol) of 1,3-bis(4,4,5,5-tetramethyl-1,3,2-dioxaborolan-2-yl)benzene, 0.92 g (0.8 mmol) of tetrakis(triphenylphosphine)palladium, 40 ml of 2M Na$_2$CO$_3$, 60 ml of EtOH and 130 ml toluene was degassed and placed under nitrogen, and then heated at 90° C. overnight. After finishing the reaction, the mixture was allowed to cool to room temperature. The solution was extracted with 100 mL of ethyl acetate and 300 ml of water. The organic layer was dried with anhydrous magnesium sulfate and the solvent was evaporated under reduced pressure. The residue was purified by column chromatography on silica(hexane-ethyl acetate) to give product 2.9 g (34%).

Synthesis of 2-chloro-9-phenyl-1,10-phenanthroline

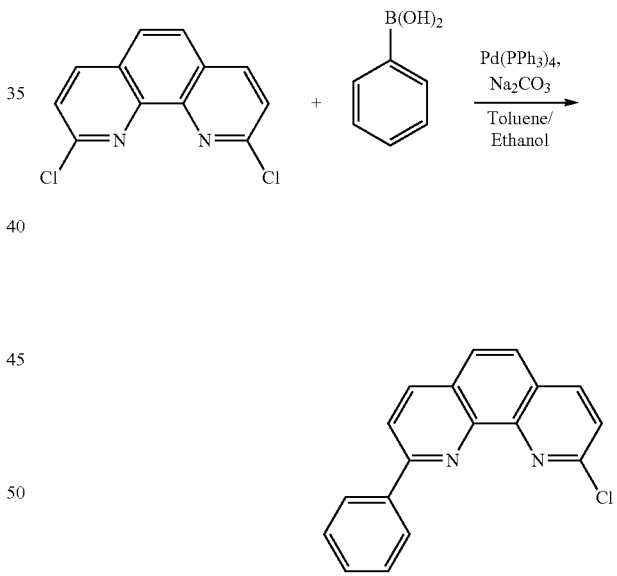

A mixture of 12.5 g (50 mmol) of 2,9-dichloro-1,10-phenanthroline, 6.1 g (50 mmol) of phenylboronic acid, 1.1 g (1 mmol) of tetrakis(triphenyl phosphine)palladium, 50 ml of 2M Na$_2$CO$_3$, 100 ml of EtOH and 150 ml toluene was degassed and placed under nitrogen, and then heated at 90° C. overnight. After finishing the reaction, the mixture was allowed to cool to room temperature. The solution was extracted with 100 mL of ethyl acetate and 500 ml of water. The organic layer was dried with anhydrous magnesium sulfate and the solvent was evaporated under reduced pressure. The residue was purified by column chromatography on silica(hexane-CH$_2$Cl$_2$) to give product 5.9 g (41%).

Synthesis of 3-(3-(9-phenyl-1,10-phenanthrolin-2-yl)phenyl)benzo[f][1,10]phenanthroline

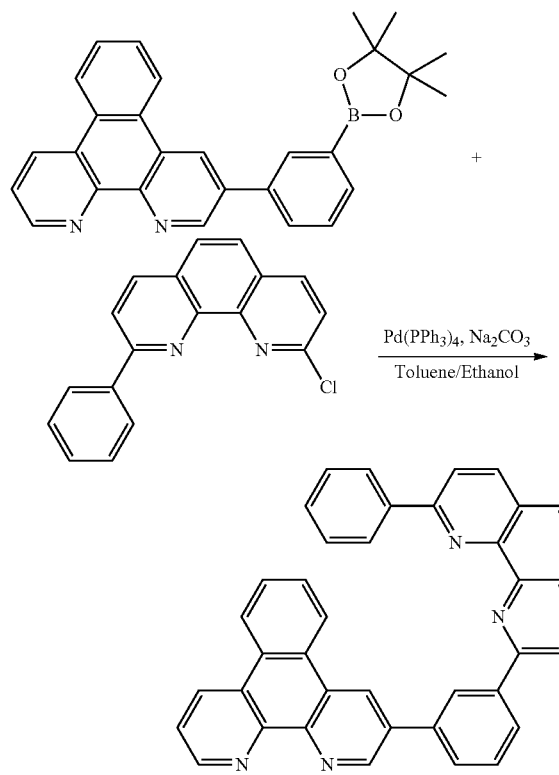

A mixture of 2.9 g (6.7 mmol) of 3-(3-(4,4,5,5-tetramethyl-1,3,2-dioxaborolan-2-yl)phenyl)benzo[f][1,10]phenanthroline, 2 g (6.7 mmol) of 2-chloro-9-phenyl-1,10-phenanthroline, 0.23 g (0.2 mmol) of tetrakis(triphenylphosphine)palladium, 2M $Na_2CO_3$ 7 ml, 10 ml of EtOH and 20 ml toluene was degassed and placed under nitrogen, and then heated at 90° C. overnight. After finishing the reaction, the mixture was allowed to cool to room temperature. Then 100 ml MeOH was added, while stirring and the precipitated product was filtered off with suction to give 3 g (yield 79%) of yellow product which was recrystallized from chloroform. MS (m/z, FAB$^+$): 560.8, $^1$H NMR (CDCl$_3$, 400 MHz): chemical shift (ppm) 9.81~9.78 (2H), 8.83 (m, 4H), 8.66~8.59 (m, 4H), 8.52~8.31 (m, 6H), 8.11~7.89 (m, 5H), 7.42~7.37 (m, 3H).

General Method of Producing Organic EL Device

ITO-coated glasses with 9~12 ohm/square in resistance and 120~160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit (10$^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material. This is achieved by co-vaporization from two or more sources.

Dipyrazino[2,3-f:2,3-]quinoxaline-2,3,6,7,10,11-hexacarbonitrile (HAT-CN) is used as hole injection layer in this organic EL device. N,N-Bis(naphthalene-1-yl)-N,N-bis(phenyl)-benzidine (NPB) is most widely used as the hole transporting layer. 10,10-Dimethyl-12-(4-(pyren-1-yl)phenyl)-10H-indeno[1,2-b]triphenylene(PT-302, US20140175384) are used as emitting host and N1,N1,N6,N6-tetram-tolylpyrene-1,6-diamine (D1) is used as blue guest. 4,7-Diphenyl-2,9-bis(4-(1-phenyl-1H-benzo[d]imidazol-2-yl)phenyl)-1,10-phenanthroline (LT-N8001, U.S. Pat. No. 7,754,348) is used as electron transporting material (ETM) to co-deposit with 5% Li in organic EL device. Bis(2-methyl-8-quinolinolate)-4-(phenylphenolato)aluminium (BAlq) is used as hole blocking layer (HBL) or phosphorescent host for phosphorescent system, tris(1-phenylisoquinoline) Iridium(III)Ir(piq)$_3$), tris(2-phenylquinoline)iridium(III)(Ir(2-phq)$_3$) are used as phosphorescent dopant. The prior art of OLED materials for producing standard organic EL device and comparable material in this invention shown its chemical structure as following:

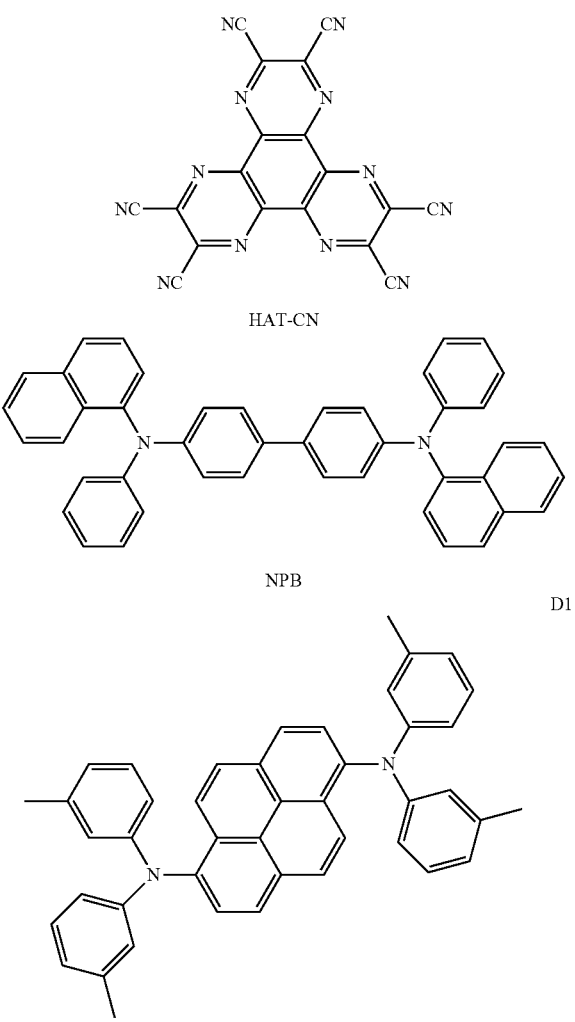

PT-312
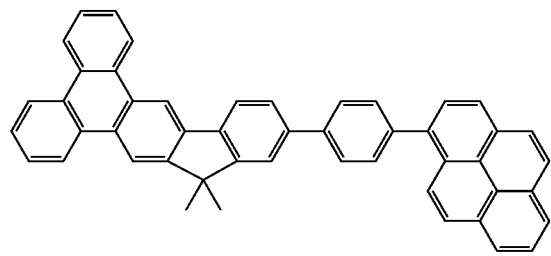
LT-N8001
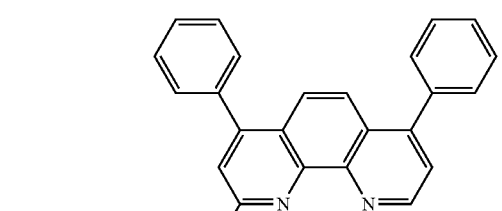
BAlq
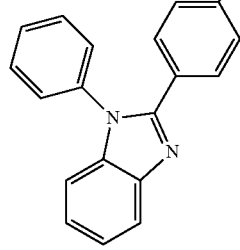
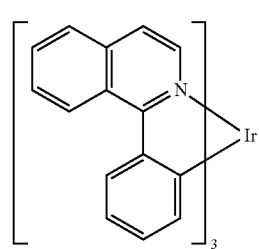
Ir(piq)₃
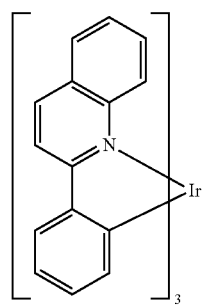
Ir(2-phq)₃
The phenanthroline-based compounds prepared from EXAMPLE 1~6 are shown its chemical structure as following:
Compound 1
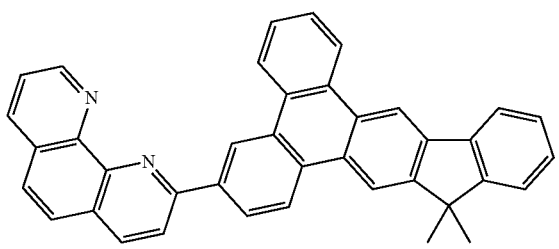
Compound 2
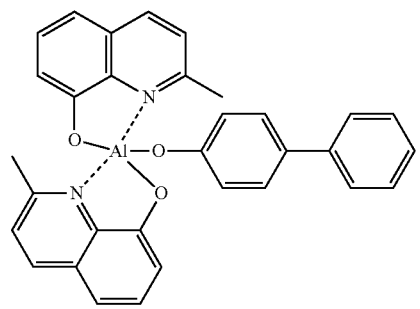
Compound 3
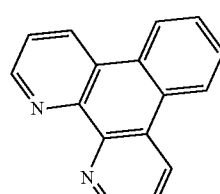
Compound 4
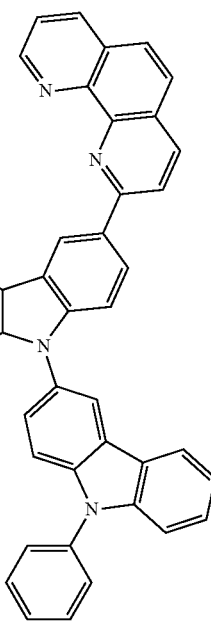

Compound 5

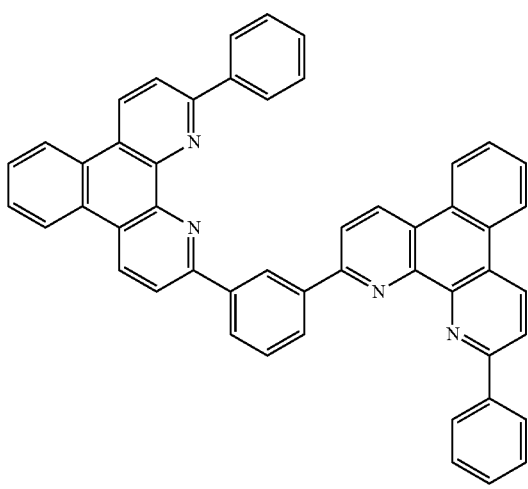

Comopound 6

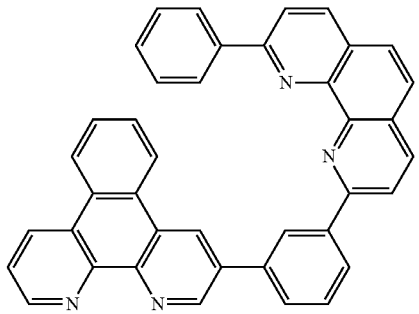

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, MgO, or $Li_2O$.

On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

EXAMPLE 7

Using a procedure analogous to the above mentioned general method, fluorescent blue-emitting organic EL device having the following device structure were produced (See FIG. 1): ITO/HAT-CN (20 nm)/NPB (130 nm)/PT-312 doped 5% D1 (30 nm)/HBL (15 nm)/ETM doped 5% Li (15 nm)/Al (160 nm). The I-V-B (at 1000 nits) and half-life time of fluorescent blue-emitting organic EL device testing report as Table 1, The half-life time is defined that the initial luminance of 1000 $cd/m^2$ has dropped to half.

TABLE 1

| HBL | ETM | Voltage (V) | Yield (cd/A) | CIE (y) | Half-lifetime (hour) |
|---|---|---|---|---|---|
| — | LT-N8001 | 4.5 | 4.8 | 0.183 | 140 |
| BAlq | LT-N8001 | 4.8 | 5.1 | 0.182 | 220 |
| Compound1 | LT-N8001 | 4.6 | 5.5 | 0.188 | 350 |
| Compound2 | LT-N8001 | 4.6 | 5.6 | 0.188 | 300 |
| Compound3 | LT-N8001 | 4.3 | 5.3 | 0.187 | 480 |
| Compound3 | Compound1 | 3.8 | 5.6 | 0.187 | 680 |
| Compound3 | Compound2 | 4.0 | 5.3 | 0.188 | 550 |
| Compound1 | Compound3 | 3.8 | 5.8 | 0.188 | 580 |
| Compound3 | Compound5 | 4.6 | 5.4 | 0.189 | 950 |
| Compound3 | Compound6 | 4.8 | 5.5 | 0.189 | 890 |

EXAMPLE 8

Using a procedure analogous to the above mentioned general method, phosphorescent emitting organic EL device having the following device structures are produced (See FIG. 1.): ITO/HAT-CN (20 nm)/NPB (50 nm)/phosphorescent host+12% dopant (30 nm)/Balq (15 nm)/LT-N8001 doped 5% Li (15 nm)/Al (160 nm). The I-V-B (at 1000 nits) and half-life time of phosphorescent emitting organic EL device testing report as Table 2. The half-life time is defined that the initial luminance of 3000 $cd/m^2$ has dropped to half.

TABLE 2

| Phosphorescent host + 12% dopant | Voltage (V) | Yield (cd/A) | Device color | Half-lifetime (hour) |
|---|---|---|---|---|
| BAlq + 12%Ir(piq)$_3$ | 4.5 | 7.5 | red | 650 |
| BAlq + 12%Ir(phq)$_3$ | 5.1 | 21.5 | yellow | 660 |
| Compound4 + 12%Ir(piq)$_3$ | 4.2 | 11.9 | red | 810 |
| Compound4 + 12%Ir(phq)$_3$ | 3.7 | 29.7 | yellow | 1230 |

In the above preferred embodiments for organic EL device test report (see Table 1 and Table 2), we show that the phenanthroline-based compound formula (I) in the present invention used as hole blocking material/electron transport material or phosphorescent host display good performance than the prior art of OLED materials To sum up, the present invention discloses a phenanthroline-based compound which can be used for organic EL device is disclosed. The mentioned phenanthroline-based compound are represented by the following formula (I):

formula(I)

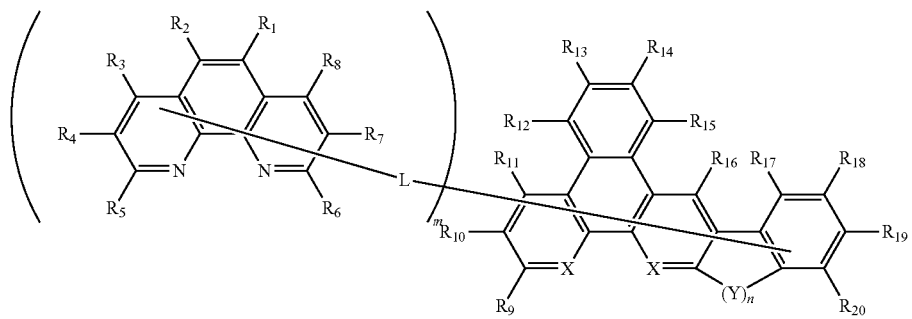

Wherein L represent a single bond, a substituted or unsubstituted arylene group having 6 to 30 ring carbon atoms, or a substituted or unsubstituted heterarylene group having 3 to 30 ring carbon atoms. m represent an integer of 1 to 3. n represent an integer of 0 or 1, X represent carbon or nitrogen atom. Y is a divalent bridge selected from the atom or group consisting from O, S, C(R$_{21}$)(R$_{22}$), N—HAr, Si(R$_{23}$)(R$_{24}$). R$_1$ and R$_2$ may be bonded each other to form a benzene ring and adjacent to phenanthroline skeleton to form a substituted or unsubstituted benzo[f][1,10]phenanthroline ring. R$_1$ to R$_{24}$ independently selected from the group consisting of a hydrogen atom, alkyl group having 1 to 20 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 3 to 30 carbon atoms. HAr represent a substituted or unsubstituted heteroaryl group having 3 to 40 carbon atoms.

Obvious many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

The invention claimed is:

1. A phenanthroline-based compound with a general formula (I) as following:

formula(I)

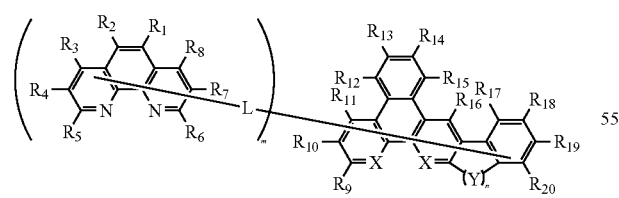

wherein:
L represent a single bond, a substituted or unsubstituted phenylene group and is bonded to the phenanthroline skeleton at the R$_5$ position and to the indenotriphenylene skeleton at one of the R$_9$, R$_{10}$, R$_{18}$ and R$_{19}$ position of indenotriphenylene skeleton;
m represent an integer of 1 to 3;
n represent an integer of 0 or 1;
X represent carbon or nitrogen atom;
Y is a divalent bridge selected from the atom or group consisting from O, S, C(R$_{21}$)(R$_{22}$), N-HAr, Si(R$_{23}$)(R$_{24}$);
R$_1$ and R$_2$ may be bonded each other to form a benzene ring which together with the phenanthroline skeleton forms a substituted or unsubstituted benzo [f][1,10] phenanthroline ring;
R$_1$ to R$_{24}$, if present, are independently selected from the group consisting of a hydrogen atom, alkyl group having 1 to 20 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms; and
HAr represent a substituted or unsubstituted heteroaryl group having 3 to 40 carbon atoms.

2. The phenanthroline-based compound according to claim 1, which is represented by one of the following formula (I-1) to formula (I-4):

formula(I-1)

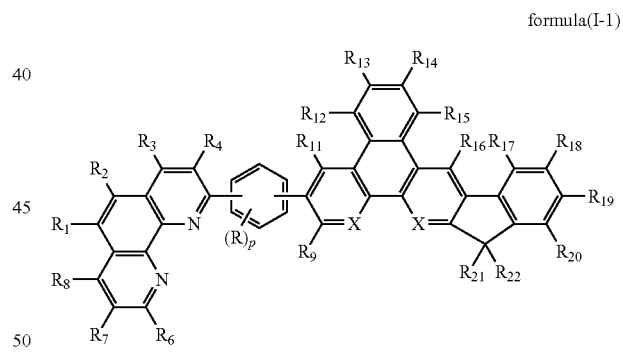

formula(I-2)

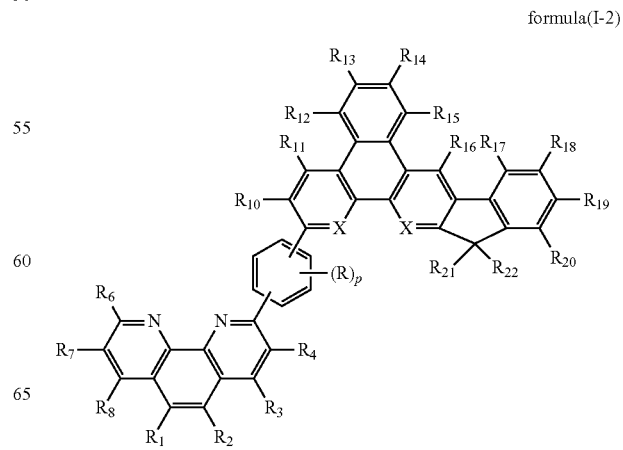

-continued

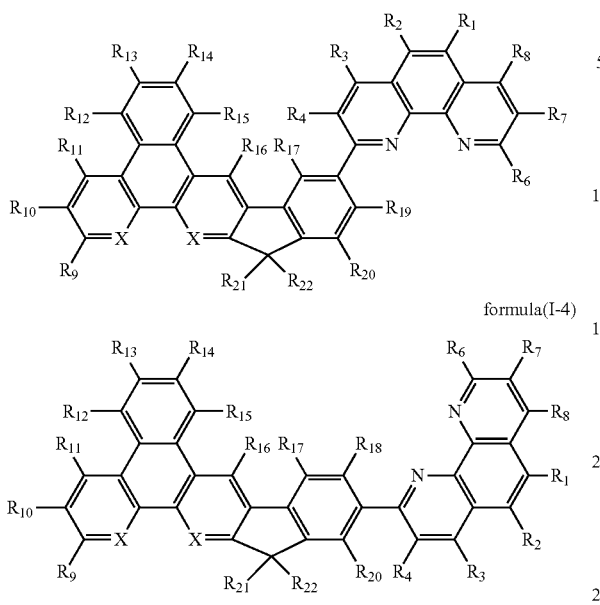

formula(I-3)

formula(I-4)

wherein R have the same meaning as $R_1$; p represent an integer of 0 to 4; X, Y, and $R_1$ to $R_{22}$ have the meaning given in claim 1.

3. The phenanthroline-based compound according to claim 1, which is represented by the following formula (I-5) or formula (I-6):

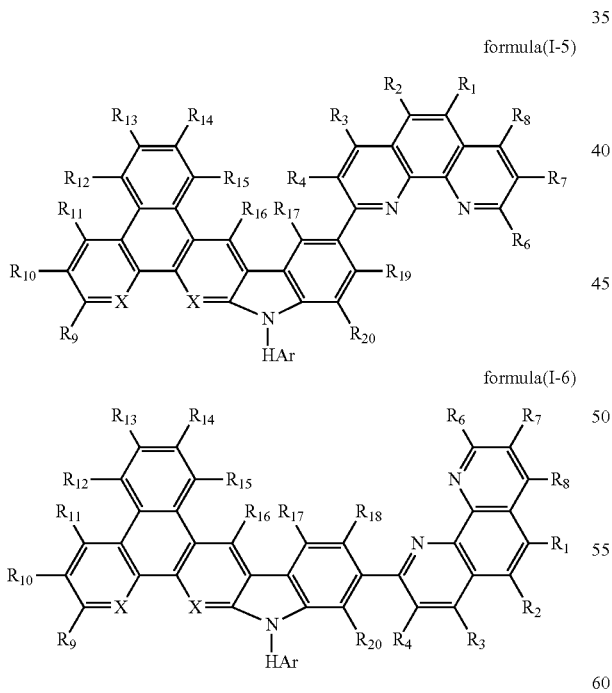

formula(I-5)

formula(I-6)

wherein HAr represent a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, or a substituted or unsubstituted diazinyl group.

4. The phenanthroline-based compound according to claim 3, wherein HAr is selected from the group consisting of the followings:

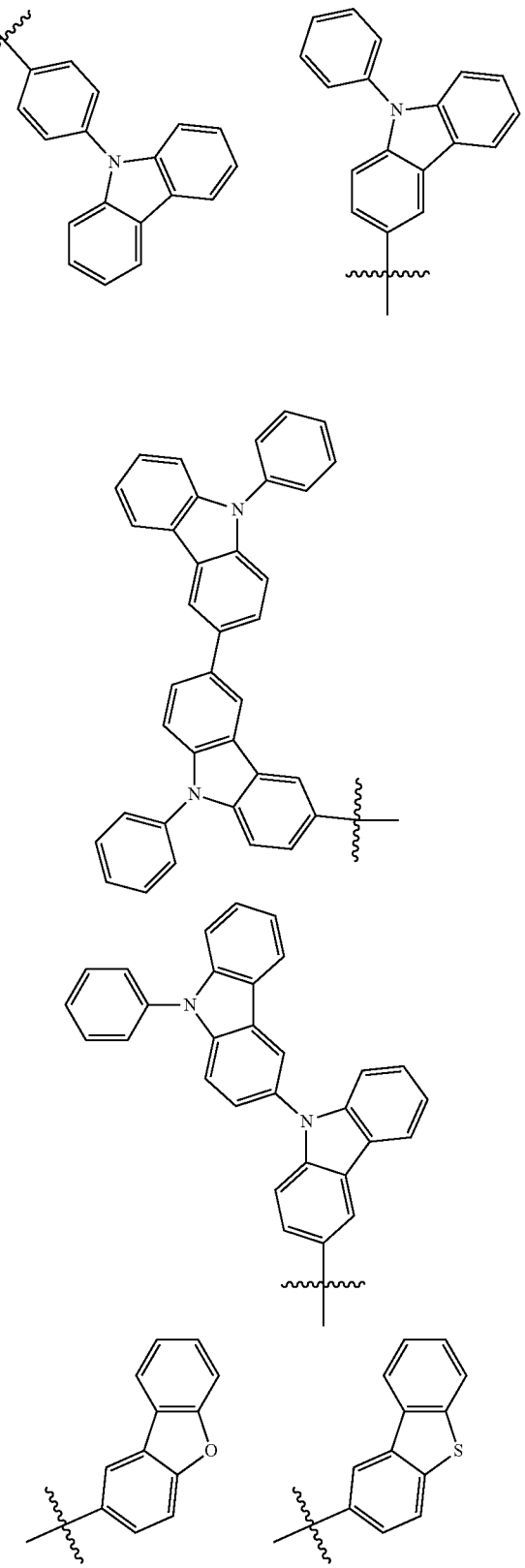

-continued
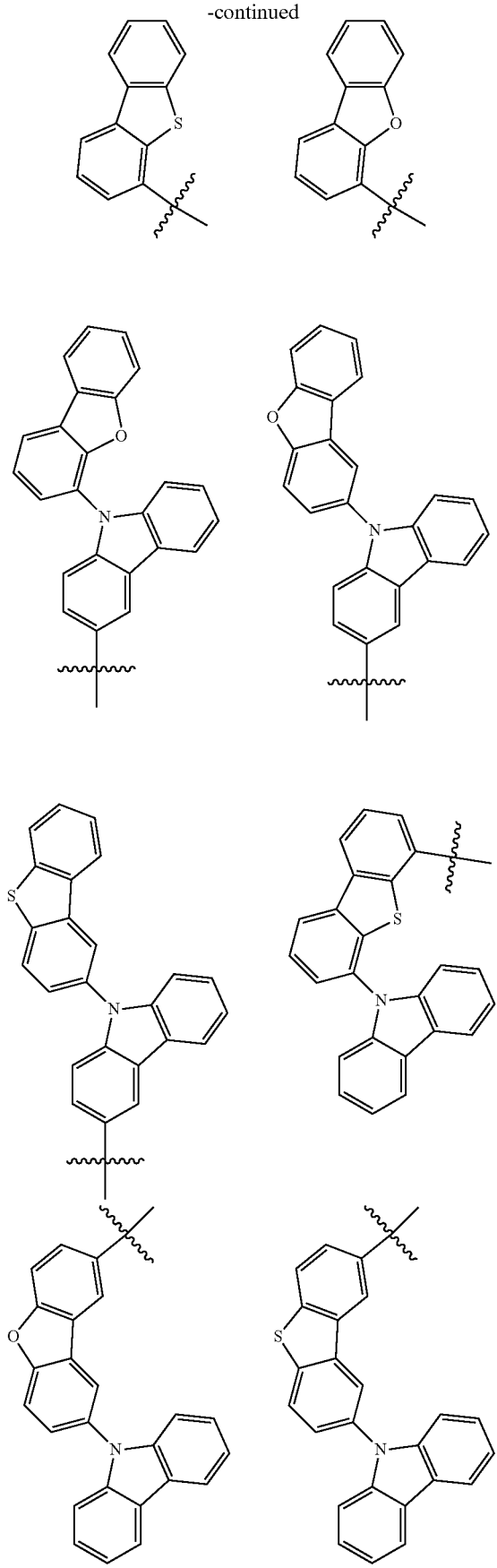
-continued
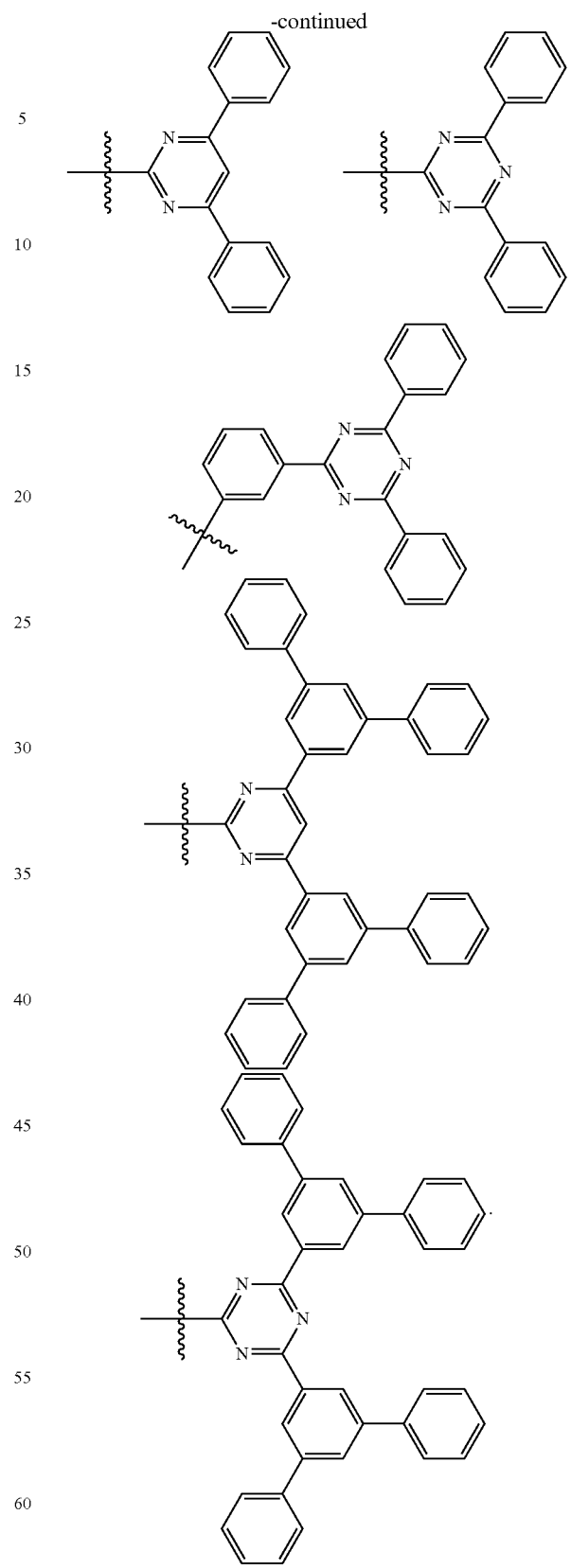
5. A organic EL device comprising a pair of electrodes consisting of a cathode and an anode and between the pairs of electrodes comprising at least a layer of material with a general formula (I) as following:

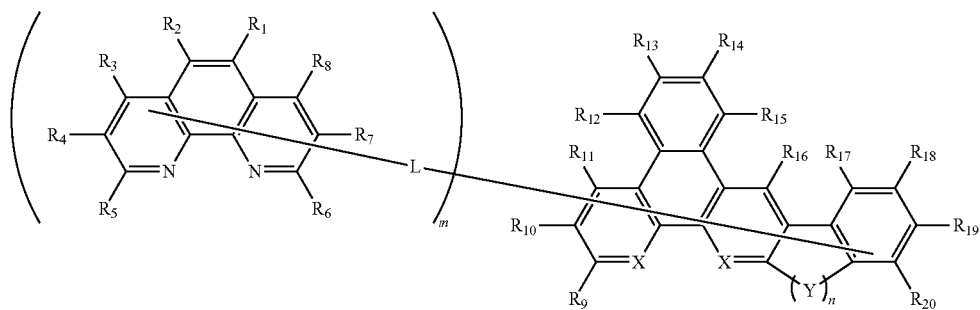

formula(I)

wherein:

L represent a single bond, a substituted or unsubstituted phenylene group and is bonded to the phenanthroline skeleton at the $R_5$ position and to the indenotriphenylene skeleton at one of the $R_9$, $R_{10}$, $R_{18}$ and $R_{19}$ position of indenotriphenylene skeleton;

m represent an integer of 1 to 3;

n represent an integer of 0 or 1;

X represent carbon or nitrogen atom;

Y is a divalent bridge selected from the atom or group consisting from O, S, $C(R_{21}R_{22})$, N-HAr, $Si(R_{23})(R_{24})$;

$R_1$ and $R_2$ may be bonded each other to form a benzene ring which together with the phenanthroline skeleton forms a substituted or unsubstituted benzo [f][1,10] phenanthroline ring;

$R_1$ to $R_{24}$, if present, are independently selected from the group consisting of a hydrogen atom, alkyl group having 1 to 20 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms; and HAr represent a substituted or unsubstituted heteroaryl group having 3 to 40 carbon atoms.

6. The organic EL device according to claim 5, comprising between the pairs of electrodes at least a layer of material with one of the following formula (I-1) to formula (I-4):

formula(I-1)

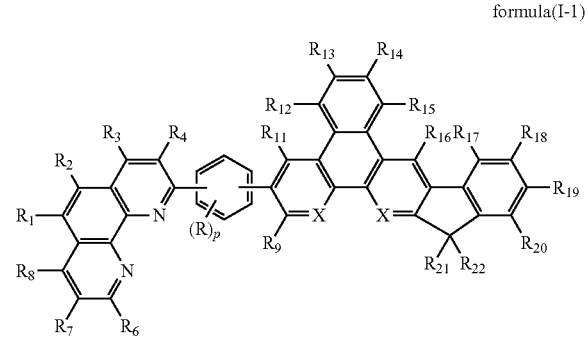

-continued formula(I-2)

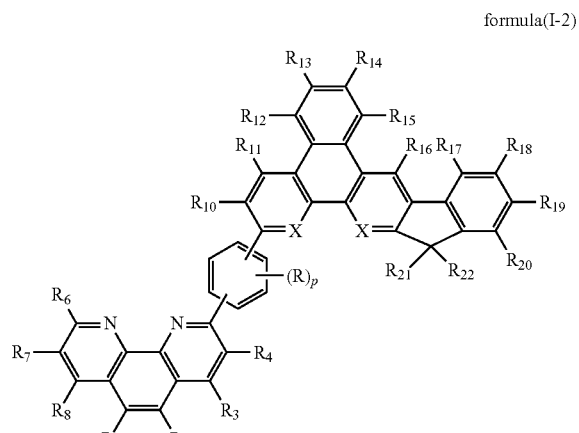

formula(I-3)

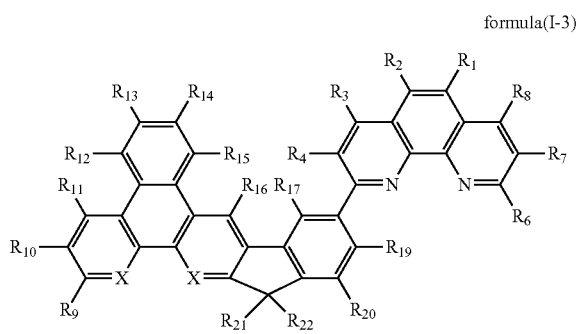

formula(I-4)

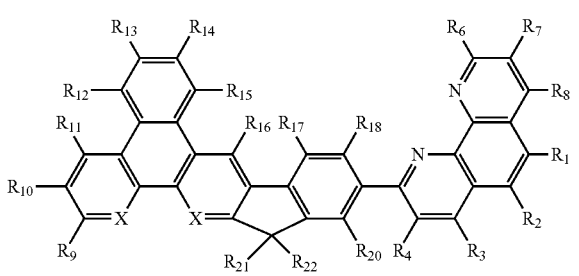

wherein R have the same meaning as $R_1$; p represent an integer of 0 to 4; X, Y, and $R_1$ to $R_{22}$ have the meaning given in claim 1.

7. The organic EL device according to claim 5, comprising between the pairs of electrodes at least a layer of material with the following formula (I-5) or formula (I-6):

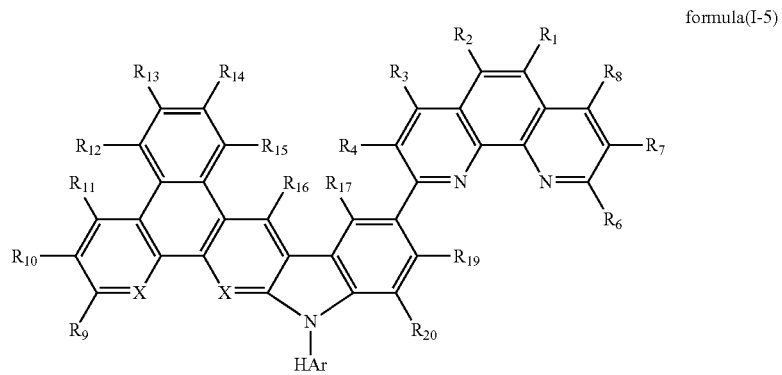

formula(I-5)

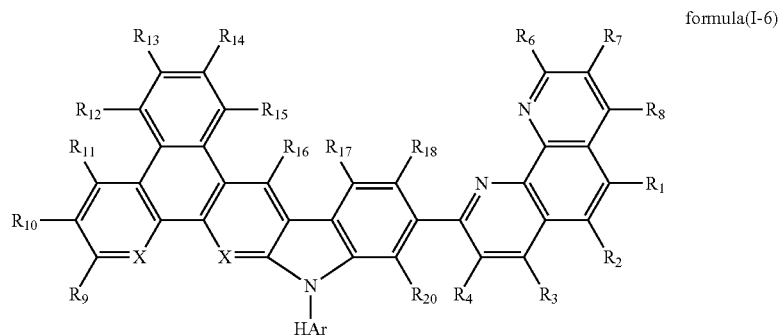

formula(I-6)

wherein HAr represent a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, or a substituted or unsubstituted diazinyl group.

8. The organic EL device according to claim 7, wherein HAr is selected from the group consisting of the followings:

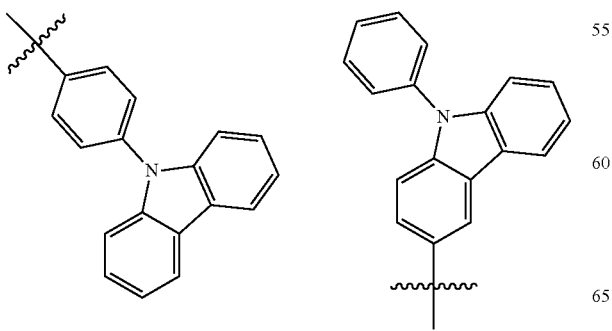

-continued

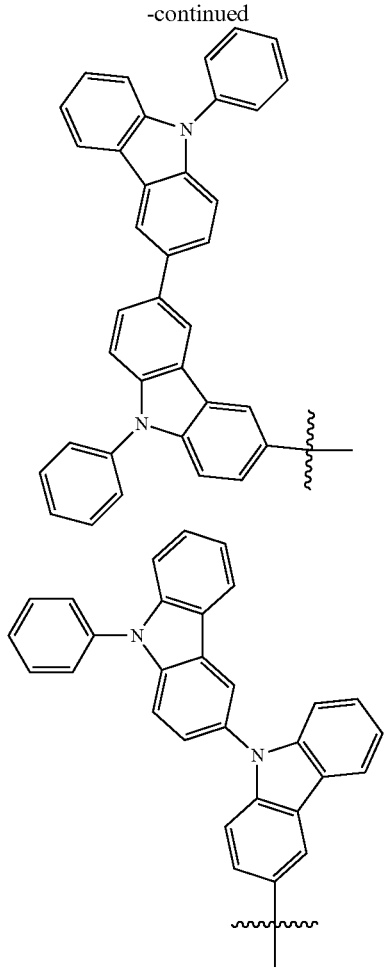

-continued
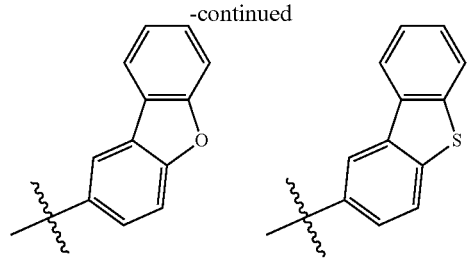
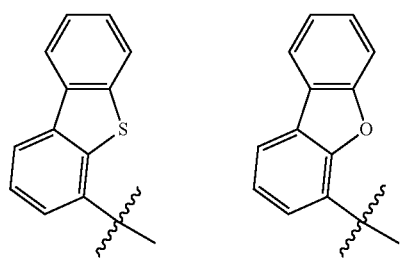
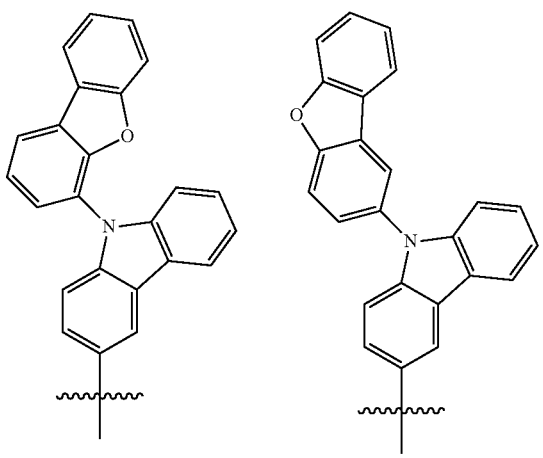
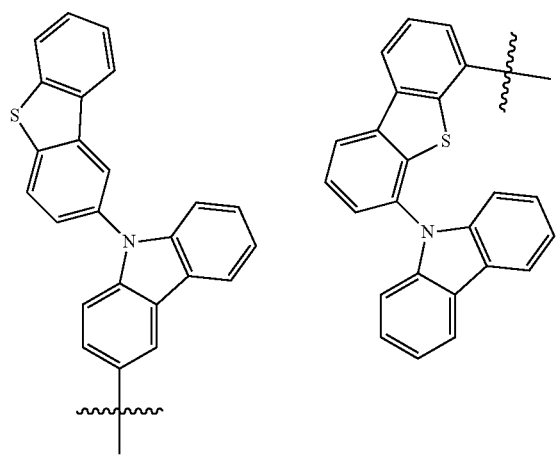
-continued
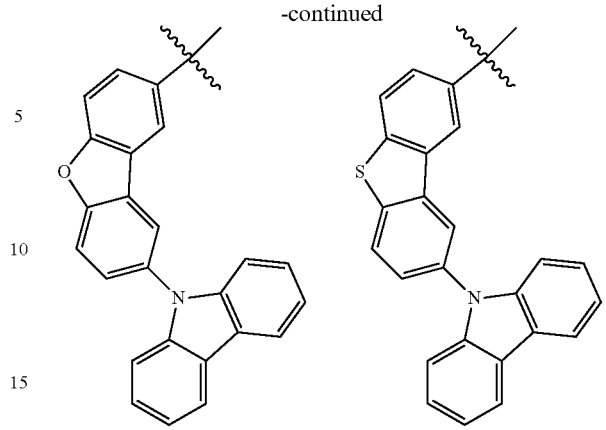
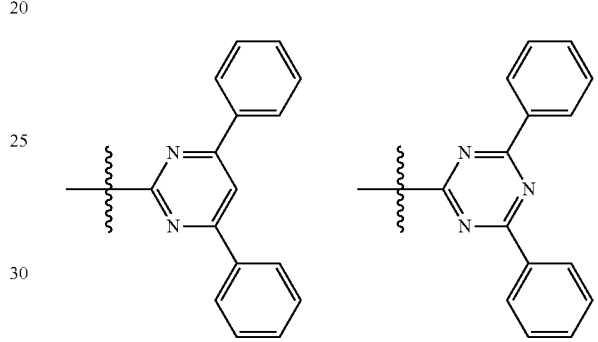
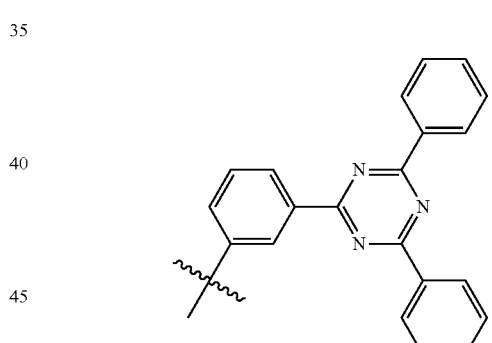
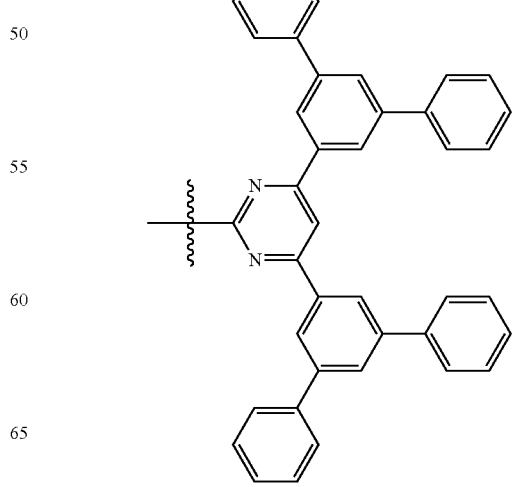

-continued

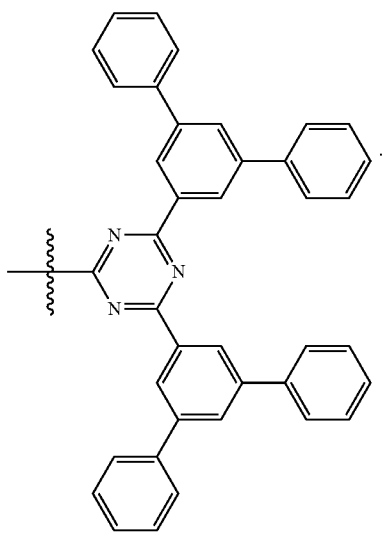

9. The organic EL device according to claim 5, wherein the material with the formula (I) is used as hole blocking material, electron transport material, or phosphorescent host for organic EL device.

10. The organic EL device according to claim 6, wherein the material with one of the formula (I-1) or formula (I-4) is used as hole blocking material for organic EL device.

11. The organic EL device according to claim 6, wherein the material with one of the formula (I-1) or formula (I-4) is used as electron transport material for organic EL device.

12. The organic EL device according to claim 7, wherein the material with the formula (I-5) or formula (I-6) is used as phosphorescent host for organic EL device.

* * * * *